United States Patent
Sato

(10) Patent No.: US 10,174,167 B2
(45) Date of Patent: Jan. 8, 2019

(54) POLYIMIDE RESIN

(71) Applicant: MITSUBISHI GAS CHEMICAL COMPANY, INC., Chiyoda-ku (JP)

(72) Inventor: Yuuki Sato, Kanagawa (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 15/505,784

(22) PCT Filed: Mar. 10, 2016

(86) PCT No.: PCT/JP2016/057511
§ 371 (c)(1),
(2) Date: Feb. 22, 2017

(87) PCT Pub. No.: WO2016/147997
PCT Pub. Date: Sep. 22, 2016

(65) Prior Publication Data
US 2017/0275425 A1    Sep. 28, 2017

(30) Foreign Application Priority Data

Mar. 19, 2015  (JP) .................. 2015-056249
Nov. 16, 2015  (JP) .................. 2015-224147

(51) Int. Cl.
C08G 73/10    (2006.01)
C08J 5/18     (2006.01)
G01N 21/35    (2014.01)

(52) U.S. Cl.
CPC ..... *C08G 73/1007* (2013.01); *C08G 73/1017* (2013.01); *C08G 73/1042* (2013.01); *C08G 73/1075* (2013.01); *C08G 73/1082* (2013.01); *C08J 5/18* (2013.01); *C08J 2379/08* (2013.01); *G01N 2021/3595* (2013.01)

(58) Field of Classification Search
CPC .......................... C09D 179/08; C08G 73/1042
See application file for complete search history.

(56) References Cited

U.S. PATENT DOCUMENTS

| 8,927,678 B2* | 1/2015 | Sato ............. C08G 73/10 428/458 |
| 2005/0080229 A1 | 4/2005 | Deets et al. |
| 2014/0200325 A1* | 7/2014 | Sato ............. C08G 73/10 528/188 |

FOREIGN PATENT DOCUMENTS

| CN | 103732655 A | 4/2014 |
| CN | 103890042 A | 6/2014 |
| JP | 7-173300 A | 7/1995 |
| JP | 10-195195 | 7/1998 |
| JP | 2002-179913 A | 6/2002 |
| JP | 2005-28524 A | 2/2005 |
| JP | 2005-187768 A | 7/2005 |
| JP | 2005-249952 A | 9/2005 |
| JP | 2007-238818 | 9/2007 |
| JP | 2009-521560 A | 6/2009 |
| JP | 2011-201952 A | 10/2011 |
| JP | 2013-10255 A | 1/2013 |
| JP | 2014-24894 | 2/2014 |
| JP | 2016-138236 | 8/2016 |
| WO | 2013/118704 A1 | 8/2013 |
| WO | WO 2013/118704 * | 8/2013 |
| WO | 2015/020016 A1 | 2/2015 |
| WO | 2015/020020 A1 | 2/2015 |

OTHER PUBLICATIONS

International Search Report dated May 10, 2016 in PCT/JP2016/057511 filed Mar. 10, 2016.
"AURUM Technical Information/G-06 AURUM injection molding conditions," [online], Jan. 15, 2004, 1 page, [searched on Jun. 28, 2013], Internet URL.http://jp.mitsuichem.com/info/aurum/aurum_pdf/G_06.pdf.
Yudin, Vladimir E. et al., "The Nucleating Effect of Carbon Nanotubes on Crystallinity in R-BAPB-Type Thermoplastic Polyimide," Macromolecular Rapid Communications, vol. 26, 2005, pp. 885-888.
"Latest Polyimides—Fundamentals and Applications (newly revised)," Japan Polyimide & Aromatic Polymers Research Group, NTS Inc., Aug. 2010, pp. 174-177.
Extended European Search Report dated Oct. 16, 2018, in European Patent Application No. 16764827.8.

* cited by examiner

*Primary Examiner* — Gregory Listvoyb
(74) *Attorney, Agent, or Firm* — Oblon, McClelland, Maier & Neustadt, L.L.P.

(57) ABSTRACT

A polyimide resin containing a repeating structural unit represented by the following formula (1) and a repeating structural unit represented by the following formula (2), a content ratio of the repeating structural unit of formula (1) with respect to the total of the repeating structural unit of formula (1) and the repeating structural unit of formula (2) being 20 to 70 mol %, and the polyimide resin having a chain aliphatic group having from 5 to 14 carbon atoms at an end thereof:
wherein $R_1$ represents a divalent group having from 6 to 22 carbon atoms containing at least one alicyclic hydrocarbon structure; $R_2$ represents a divalent chain aliphatic group having from 5 to 16 carbon atoms; and $X_1$ and $X_2$ each independently represent a tetravalent group having from 6 to 22 carbon atoms containing at least one aromatic ring.

12 Claims, No Drawings

POLYIMIDE RESIN

CROSS-REFERENCE TO RELATED APPLICATIONS

This application is a National Stage of PCT/JP2016/057511, which was filed on Mar. 10, 2016. This application is based upon and claims the benefit of priority to Japanese Application No. 2015-015249, which was filed on Mar. 19, 2015, and to Japanese Application No 2015-224147, which was filed on Nov. 16, 2015.

TECHNICAL FIELD

The present invention relates to a thermoplastic polyimide resin.

BACKGROUND ART

A polyimide resin is a useful engineering plastic that has high thermal stability, high strength and high solvent resistance due to rigidity, resonance stabilization and firm chemical bond of the molecular chain thereof, and is being applied to a wide range of fields. A polyimide resin having crystallinity is further enhanced in the heat resistance, the strength and the chemical resistance thereof, and thus is expected for applications as alternatives of metals or the like. While a polyimide resin has high heat resistance, however, it has the problems of exhibiting no thermoplasticity and having low molding process ability.

Vespel (registered trademark), a highly heat-resistant resin, is known as a polyimide molding material (PTL 1). This resin is difficult to process by molding due to its very low flowability even at a high temperature, and is also disadvantageous in terms of cost because it requires molding under conditions of a high temperature and a high pressure for a prolonged period of time. In contrast to this, a resin having a melting point and flowability at a high temperature, such as a crystalline resin, may be processed by molding easily and inexpensively.

Thus, a polyimide resin having thermoplasticity has been reported in recent years. Such a thermoplastic polyimide resin is excellent in molding processability in addition to the original heat resistance of the polyimide resin. The thermoplastic polyimide resin is therefore applicable to a molded article for use in an inhospitable environment to which nylon or polyester, a general purpose thermoplastic resin, is inapplicable.

Aurum (registered trademark) or the like is known as a thermoplastic polyimide resin (NPL 1). Aurum is, however, limited in terms of an available apparatus because of having a high melting point and requiring a molding temperature of generally 400° C. or more.

A method using a long linear aliphatic diamine as a raw material diamine is one of the methods for improving the molding processability of the polyimide resin, i.e., the methods for decreasing the melting point of the polyimide resin (NPL 2). This reduces the rigidity of the polyimide resin, and thus also decreases the melting point. This method, however, might decrease the glass transition temperature along with the decrease of the melting point, and in particular, might reduce the strength at a high temperature. Another problem of this method is difficult synthesis of a polyimide resin using a raw material diamine composed mainly of an aliphatic diamine.

In view of the above problems, a polyimide resin satisfying both molding processability and heat resistance and a composition comprising the polyimide resin are developed (PTLs 5 and 6).

CITATION LIST

Patent Literature

PTL 1: JP-A-2005-28524
PTL 2: JP-A-H07-173300
PTL 3: JP-A-2013-10255
PTL 4: JP-A-2005-249952
PTL 5: WO2013/118704
PTL 6: WO2015/020020

Non Patent Literature

NPL 1: "AURUM Technical Information/G-06 AURUM injection molding conditions", [online], Jan. 15, 2004 [searched on Jun. 28, 2013], Internet <URL: http://jp.mit-suichem.com/info/aurum/aurum_pdf/G_06.pdf>
NPL 2: Macromol. Rapid. Commun., 885, 26, 2005
NPL 3: "Latest Polyimides-Fundamentals and Applications (newly revised)" edited by the Japan Polyimide & Aromatic Polymers Research Group, published by NTS Inc., issued on August 2010, p. 175-176

SUMMARY OF INVENTION

Technical Problem

The polyimide resin, however, is demanded to be further enhanced in heat aging resistance.

An object of the present invention is to provide a novel polyimide resin excellent in molding processability and heat resistance, and particularly excellent in heat aging resistance.

Solution to Problem

The present inventors have found that the aforementioned object can be attained by a polyimide resin containing particular different polyimide structural units combined at a particular ratio and having a particular group at the end thereof.

That is, the present invention provides a polyimide resin containing a repeating structural unit represented by the following formula (1) and a repeating structural unit represented by the following formula (2), a content ratio of the repeating structural unit of formula (1) with respect to the total of the repeating structural unit of formula (1) and the repeating structural unit of formula (2) being 20 to 70 mol %, and the polyimide resin having a chain aliphatic group having from 5 to 14 carbon atoms at an end thereof:

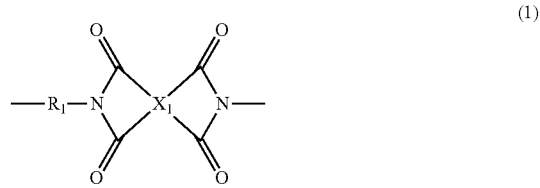

-continued

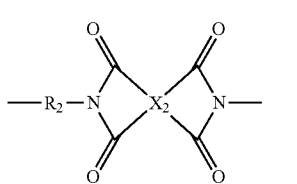

wherein $R_1$ represents a divalent group having from 6 to 22 carbon atoms containing at least one alicyclic hydrocarbon structure; $R_2$ represents a divalent chain aliphatic group having from 5 to 16 carbon atoms; and $X_1$ and $X_2$ each independently represent a tetravalent group having from 6 to 22 carbon atoms containing at least one aromatic ring.

Advantageous Effects of Invention

The polyimide resin of the present invention is excellent in molding processability, heat resistance and heat aging resistance. For example, even if a film comprising the polyimide resin is stored under a high-temperature environment of 200° C. or more for several days, the molecular weight retention rate is less decreased to allow the mechanical strength (toughness) of the film to be kept. The polyimide resin is preferably used in an application where heat aging resistance is required, for example, a member for use in automobiles, such as a gear, a tube and a pipe, a sliding member for use in a copier and the like, an industrial piping, an electronic member, and a covering material.

DESCRIPTION OF EMBODIMENTS

[Polyimide Resin]

The polyimide resin of the present invention contains a repeating structural unit represented by the following formula (1) and a repeating structural unit represented by the following formula (2), the content ratio of the repeating structural unit of formula (1) with respect to the total of the repeating structural unit of formula (1) and the repeating structural unit of formula (2) being 20 to 70 mol %, and the polyimide resin having a chain aliphatic group having from 5 to 14 carbon atoms at the end thereof:

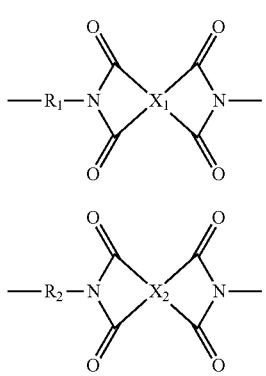

wherein $R_1$ represents a divalent group having from 6 to 22 carbon atoms containing at least one alicyclic hydrocarbon structure; $R_2$ represents a divalent chain aliphatic group having from 5 to 16 carbon atoms; and $X_1$ and $X_2$ each independently represent a tetravalent group having from 6 to 22 carbon atoms containing at least one aromatic ring.

The polyimide resin of the present invention contains particular different polyimide structural units combined at the aforementioned particular ratio and has a predetermined group at the end thereof, and therefore is excellent in molding processability and heat resistance and furthermore excellent in heat aging resistance.

The repeating structural unit of formula (1) will be described in detail below.

$R_1$ represents a divalent group having from 6 to 22 carbon atoms containing at least one alicyclic hydrocarbon structure. The alicyclic hydrocarbon structure herein means a ring derived from an alicyclic hydrocarbon compound, and the alicyclic hydrocarbon compound may be either saturated or unsaturated and may be either monocyclic or polycyclic.

Examples of the alicyclic hydrocarbon structure include a cycloalkane ring, such as a cyclohexane ring, a cycloalkene ring, such as cyclohexene, a bicycloalkane ring, such as a norbornane ring, and a bicycloalkene ring, such as norbornene, but the alicyclic hydrocarbon structure is not limited thereto. Among these, a cycloalkane ring is preferred, a cycloalkane ring having from 4 to 7 carbon atoms is more preferred, and a cyclohexane ring is further preferred.

$R_1$ has from 6 to 22 carbon atoms, and preferably from 8 to 17 carbon atoms.

$R_1$ contains at least one alicyclic hydrocarbon structure, and preferably from 1 to 3 alicyclic hydrocarbon structures.

$R_1$ is preferably a divalent group represented by the following formula (R1-1) or (R1-2):

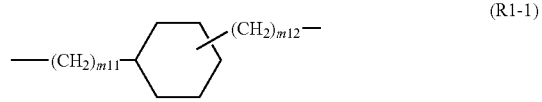

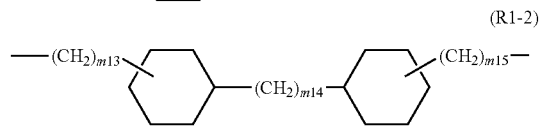

wherein $m_{11}$ and $m_{12}$ each independently represent an integer of 0-2, and preferably 0 or 1; and $m_{13}$ to $m_{15}$ each independently represent an integer of 0-2, and preferably 0 or 1.

$R_1$ is particularly preferably a divalent group represented by the following formula (R1-3):

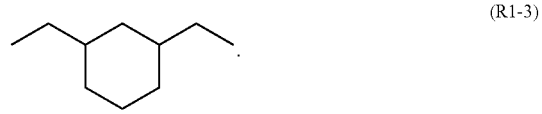

In the divalent group represented by the formula (R1-3), the conformation of the two methylene groups with respect to the cyclohexane ring may be either cis or trans, and the ratio of cis and trans may be an arbitrary value.

$X_1$ is a tetravalent group having from 6 to 22 carbon atoms containing at least one aromatic ring. The aromatic ring may be either a monocyclic ring or a condensed ring, and examples thereof include a benzene ring, a naphthalene ring, an anthracene ring and a tetracene ring, but the aromatic ring is not limited thereto. Among these, a benzene ring and a naphthalene ring are preferred, and a benzene ring is more preferred.

$X_1$ has from 6 to 22 carbon atoms, and preferably has from 6 to 18 carbon atoms.

$X_1$ contains at least one aromatic ring, and preferably contains from 1 to 3 aromatic rings.

$X_1$ is preferably a tetravalent group represented by one of the following formulae (X-1) to (X-4):

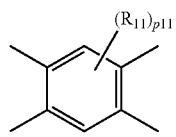
(X-1)

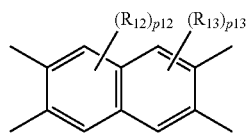
(X-2)

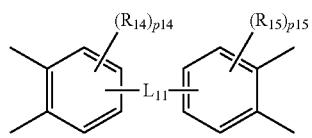
(X-3)

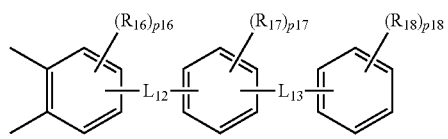
(X-4)

wherein $R_{11}$ to $R_{18}$ each independently represent an alkyl group having from 1 to 4 carbon atoms; $p_{11}$ to $p_{13}$ each independently represent an integer of 0-2, and preferably 0; $p_{14}$, $p_{15}$, $p_{16}$ and $p_{18}$ each independently represent an integer of 0-3, and preferably 0; $p_{17}$ represents an integer of 0-4, and preferably 0; and $L_{11}$ to $L_{13}$ each independently represent a single bond, an ether group, a carbonyl group or an alkylene group having from 1 to 4 carbon atoms.

$X_1$ is a tetravalent group having from 6 to 22 carbon atoms containing at least one aromatic ring, and therefore $R_{12}$, $R_{13}$, $p_{12}$ and $p_{13}$ in the formula (X-2) are selected in such a manner that the tetravalent group represented by the formula (X-2) has from 6 to 22 carbon atoms.

Similarly, $L_{11}$, $R_{14}$, $R_{15}$, $p_{14}$ and $p_{15}$ in the formula (X-3) are selected in such a manner that the tetravalent group represented by the formula (X-3) has from 6 to 22 carbon atoms, and $L_{12}$, $L_{13}$, $R_{16}$, $R_{17}$, $R_{18}$, $p_{16}$, $p_{17}$ and $p_{18}$ in the formula (X-4) are selected in such a manner that the tetravalent group represented by the formula (X-4) has from 6 to 22 carbon atoms.

$X_1$ is particularly preferably a tetravalent group represented by the following formula (X-5) or (X-6):

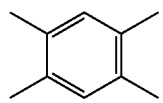
(X-5)

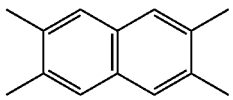
(X-6)

Next, the repeating structural unit of formula (2) will be described in detail below.

$R_2$ represents a divalent chain aliphatic group having from 5 to 16 carbon atoms, preferably from 5 to 14 carbon atoms, more preferably from 5 to 12 carbon atoms. The chain aliphatic group herein means a group derived from a chain aliphatic compound, and the chain aliphatic compound may be either saturated or unsaturated, may be in the form of either linear or branched chain, and may contain a hetero atom, such as an oxygen atom.

$R_2$ preferably represents an alkylene group having from 5 to 16 carbon atoms, more preferably an alkylene group having from 5 to 14 carbon atoms, further preferably an alkylene group having from 5 to 12 carbon atoms, particularly preferably an alkylene group having from 6 to 12 carbon atoms, more preferably an alkylene group having from 6 to 10 carbon atoms. The alkylene group may be either a linear alkylene group or a branched alkylene group, and is preferably a linear alkylene group.

$R_2$ particularly preferably represents at least one selected from the group consisting of a hexamethylene group, an octamethylene group and a decamethylene group.

Another preferred embodiment of $R_2$ is a divalent chain aliphatic group having from 5 to 16 carbon atoms containing an ether group. The divalent chain aliphatic group preferably has from 5 to 14 carbon atoms, more preferably from 5 to 12 carbon atoms. Preferred examples of the group include a divalent group represented by the following formula (R2-1) or (R2-2):

$$-(CH_2)_{m21}-O-(CH_2)_{m22}- \quad (R2\text{-}1)$$

$$-(CH_2)_{m23}-O-(CH_2)_{m24}-O-(CH_2)_{m25}- \quad (R2\text{-}2)$$

wherein $m_{21}$ and $m_{22}$ each independently represent an integer of 1-15, preferably 1-13, more preferably 1-11, and further preferably 2-6; and $m_{23}$ to $m_{25}$ each independently represent an integer of 1-14, preferably 1-12, more preferably 1-10, and further preferably 2-4.

$R_2$ represents a divalent chain aliphatic group having from 5 to 16 carbon atoms (preferably from 5 to 14 carbon atoms, more preferably from 5 to 12 carbon atoms), and therefore $m_{21}$ and $m_{22}$ in the formula (R2-1) are selected so that the divalent group represented by the formula (R2-1) has from 5 to 16 carbon atoms (preferably from 5 to 14 carbon atoms, more preferably from 5 to 12 carbon atoms), i.e., $m_{21}$ $m_{22}$ is from 5 to 16 (preferably 5 to 14, more preferably 5 to 12).

Similarly, $m_{23}$ to $m_{25}$ in the formula (R2-2) are selected so that the divalent group represented by the formula (R2-2) has from 5 to 16 carbon atoms (preferably from 5 to 14 carbon atoms, more preferably from 5 to 12 carbon atoms), i.e., $m_{23}+m_{24}$ $m_{25}$ is from 5 to 16 (preferably from 5 to 14 carbon atoms, more preferably from 5 to 12 carbon atoms).

$X_2$ is defined similarly to $X_1$ in the formula (1), and preferred embodiments thereof are also the same.

The content ratio of the repeating structural unit of formula (1) with respect to the total of the repeating structural unit of formula (1) and the repeating structural unit of formula (2) is 20 to 70 mol %. In the case where the content ratio of the repeating structural unit of formula (1) is in the above-described range, the polyimide resin may also be sufficiently crystallized in an ordinary injection molding cycle. When the content ratio is less than 20 mol %, molding processability is deteriorated, and when the content ratio is more than 70 mol %, crystallinity is deteriorated to thereby result in deterioration in heat resistance.

The content ratio of the repeating structural unit of formula (1) with respect to the total of the repeating structural unit of formula (1) and the repeating structural unit of formula (2) is preferably 25 mol % or more, more preferably 30 mol % or more and further preferably 32 mol % or more in consideration of molding processability, and is preferably 65 mol % or less, more preferably 60 mol % or less and further preferably 57 mol % or less in consideration of exerting high crystallinity.

The content ratio of the total of the repeating structural unit of formula (1) and the repeating structural unit of formula (2) with respect to the total repeating units constituting the polyimide resin of the present invention is preferably from 50 to 100 mol %, more preferably from 75 to 100 mol %, further preferably from 80 to 100 mol %, and still further preferably from 85 to 100 mol %.

The polyimide resin of the present invention may further contain a repeating structural unit represented by the following formula (3). In this case, the content ratio of the repeating structural unit of formula (3) with respect to the total of the repeating structural unit of formula (1) and the repeating structural unit of formula (2) is preferably 25 mol % or less. The lower limit thereof is not particularly limited but needs to exceed 0 mol %.

The content ratio is preferably 5 mol % or more, and more preferably 10 mol % or more, in consideration of enhancement of the heat resistance, and is preferably 20 mol % or less, and more preferably 15 mol % or less, in consideration of maintenance of the crystallinity.

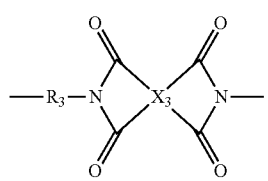

(3)

wherein $R_3$ represents a divalent group having from 6 to 22 carbon atoms containing at least one aromatic ring; and $X_3$ represents a tetravalent group having from 6 to 22 carbon atoms containing at least one aromatic ring.

$R_3$ is a divalent group having from 6 to 22 carbon atoms containing at least one aromatic ring. The aromatic ring may be either a monocyclic ring or a condensed ring, and examples thereof include a benzene ring, a naphthalene ring, an anthracene ring and a tetracene ring, but the aromatic ring is not limited thereto. Among these, a benzene ring and a naphthalene ring are preferred, and a benzene ring is more preferred.

$R_3$ has from 6 to 22 carbon atoms, and preferably has from 6 to 18 carbon atoms.

$R_3$ contains at least one aromatic ring, and preferably contains from 1 to 3 aromatic rings.

The aromatic ring may also be bonded to a monovalent or divalent electron-attracting group. Examples of the monovalent electron-attracting group include a nitro group, a cyano group, a p-toluenesulfonyl group, halogen, an alkyl halide group, a phenyl group, and an acyl group. Examples of the divalent electron-attracting group include alkylene halide groups such as alkylene fluoride groups (e.g., —C(CF$_3$)$_2$— and —(CF$_2$)$_p$— (wherein p is an integer of 1-10), as well as —CO—, —SO$_2$—, —SO—, —CONH—, and —COO—.

$R_3$ is preferably a divalent group represented by the following formula (R3-1) or (R3-2):

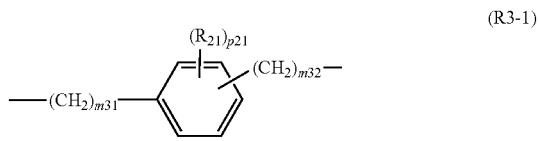

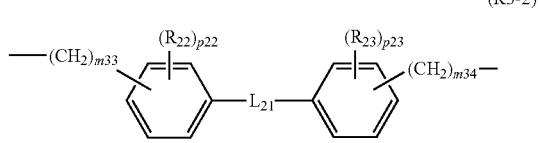

wherein $m_{31}$ and $m_{32}$ each independently represent an integer of 0-2, and preferably 0 or 1; $m_{33}$ and $m_{34}$ each independently represent an integer of 0-2, and preferably 0 or 1; $R_{21}$, $R_{22}$ and $R_{23}$ each independently represent an alkyl group having from 1 to 4 carbon atoms, an alkenyl group having from 2 to 4 carbon atoms or an alkynyl group having from 2 to 4 carbon atoms; $p_{21}$, $p_{22}$ and $p_{23}$ each represent an integer of 0-4, and preferably 0; and $L_{21}$ represents a single bond, an ether group, a carbonyl group or an alkylene group having from 1 to 4 carbon atoms.

$R_3$ is a divalent group having from 6 to 22 carbon atoms containing at least one aromatic ring, and therefore $m_{31}$, $m_{32}$, $R_{21}$ and $p_{21}$ in the formula (R3-1) are selected in such a manner that the divalent group represented by the formula (R3-1) has from 6 to 22 carbon atoms.

Similarly, $L_{21}$, $m_{33}$, $m_{31}$, $R_{22}$, $R_{23}$, $p_{22}$ and $p_{23}$ in the formula (R3-2) are selected in such a manner that the divalent group represented by the formula (R3-2) has from 12 to 22 carbon atoms.

$X_3$ is defined similarly to $X_1$ in the formula (1), and preferred embodiments thereof are also the same.

The content ratio of the repeating structural unit of formula (3) with respect to the total repeating structural units constituting the polyimide resin of the present invention is preferably 25 mol % or less. The lower limit thereof is not particularly limited but needs to exceed 0 mol %.

The content ratio is preferably 5 mol % or more, and more preferably 7 mol % or more, in consideration of enhancement of the heat resistance, and is preferably 20 mol % or less, and more preferably 15 mol % or less, in consideration of maintenance of the crystallinity.

The polyimide resin of the present invention may further contain a repeating structural unit represented by the following formula (4):

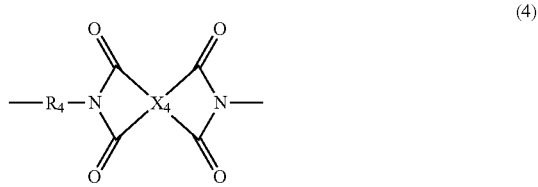

(4)

wherein $R_4$ represents a divalent group containing —SO$_2$— or —Si($R_x$)($R_y$)O—; $R_x$ and $R_y$ each independently represent a chain aliphatic group having from 1 to 3 carbon atoms, or a phenyl group; and $X_4$ represents a tetravalent group having from 6 to 22 carbon atoms containing at least one aromatic ring.

$X_4$ is defined similarly to $X_1$ in the formula (1), and preferred embodiments thereof are also the same.

The polyimide resin of the present invention is further characterized by having a chain aliphatic group having 5 to 14 carbon atoms at the end thereof.

The chain aliphatic group may be either saturated or unsaturated, and may be in the form of either linear or branched chain. The polyimide resin of the present invention is excellent in heat aging resistance because it contains the above particular group at the end thereof. Specifically, even if a film comprising the polyimide resin is stored under a high-temperature environment of 200° C. or more for several days, the molecular weight retention rate is less decreased to allow the mechanical strength (toughness) of the film to be kept.

In contrast to this, for example, when the polyimide resin has a benzyl group or a phenyl group at the end thereof, the polyimide resin is stored under a high-temperature environment of 200° C. or more to thereby result in a decrease in molecular weight retention rate and also deterioration in mechanical strength. When the chain aliphatic group at the end has 4 or less carbon atoms, a compound having a chain aliphatic group having 4 or less carbon atoms is used in order to introduce the group into the end of the polyimide resin, but the compound is not preferred because of being easily volatilized in production of the polyimide resin.

Example of the saturated chain aliphatic group having from 5 to 14 carbon atoms include an n-pentyl group, an n-hexyl group, an n-heptyl group, an n-octyl group, an n-nonyl group, an n-decyl group, an n-undecyl group, a lauryl group, an n-tridecyl group, an n-tetradecyl group, an isopentyl group, a neopentyl group, a 2-methylpentyl group, a 2-methylhexyl group, a 2-ethylpentyl group, a 3-ethylpentyl group, an isooctyl group, a 2-ethylhexyl group, a 3-ethylhexyl group, an isononyl group, a 2-ethyloctyl group, an isodecyl group, an isododecyl group, an isotridecyl group and an isotetradecyl group.

Example of the unsaturated chain aliphatic group having from 5 to 14 carbon atoms include a 1-pentenyl group, a 2-pentenyl group, a 1-hexenyl group, a 2-hexenyl group, a 1-heptenyl group, a 2-heptenyl group, a 1-octenyl group, a 2-octenyl group, a nonenyl group, a decenyl group, a dodecenyl group, a tridecenyl group and a tetradecenyl group.

Among these, the chain aliphatic group is preferably a saturated chain aliphatic group, and more preferably a saturated linear aliphatic group. The chain aliphatic group preferably has 6 or more carbon atoms, more preferably 7 or more carbon atoms and further preferably 8 or more carbon atoms, and preferably has 12 or less carbon atoms, more preferably 10 or less carbon atoms and further preferably 9 or less carbon atoms in consideration of achievement of the effect of the invention. The chain aliphatic group may be adopted singly or in combinations of two or more.

The chain aliphatic group is particularly preferably at least one selected from the group consisting of an n-octyl group, an isooctyl group, a 2-ethylhexyl group, an n-nonyl group, an isononyl group, an n-decyl group and an isodecyl group, further preferably at least one selected from the group consisting of n-octylamine, isooctylamine, 2-ethylhexylamine, n-nonylamine and isononylamine, most preferably at least one selected from the group consisting of an n-octyl group, an isooctyl group and a 2-ethylhexyl group.

The polyimide resin of the present invention preferably contains only a chain aliphatic group having from 5 to 14 carbon atoms, besides a terminal amino group and a terminal carboxyl group, at the end thereof in consideration of heat aging resistance. When a group, besides the above groups, is contained at the end, the content thereof with respect to the chain aliphatic group having from 5 to 14 carbon atoms is preferably 10 mol % or less and more preferably 5 mol % or less.

The content of the chain aliphatic group having from 5 to 14 carbon atoms in the polyimide resin is preferably 0.01 mol % or more, more preferably 0.1 mol % or more and further preferably 0.2 mol % or more based on the total 100 mol % of the total repeating structural units in the polyimide resin in consideration of exerting excellent heat aging resistance. In order that a sufficient molecular weight is ensured and good mechanical properties are achieved, the content of the chain aliphatic group having from 5 to 14 carbon atoms in the polyimide resin is preferably 10 mol % or less, more preferably 6 mol % or less and further preferably 3.5 mol % or less based on the total 100 mol % of the total repeating structural units in the polyimide resin.

The content of the chain aliphatic group having from 5 to 14 carbon atoms in the polyimide resin can be determined by depolymerization of the polyimide resin.

The polyimide resin of the present invention preferably has a melting point of 360° C. or less and a glass transition temperature of 150° C. or more. The melting point of the polyimide resin is more preferably 280° C. or more and further preferably 290° C. or more in consideration of heat resistance, and is preferably 345° C. or less, more preferably 340° C. or less and further preferably 335° C. or less in consideration of exerting high molding processability. In addition, the glass transition temperature of the polyimide resin is more preferably 160° C. or more and more preferably 170° C. or more in consideration of heat resistance, and is preferably 250° C. or less, more preferably 230° C. or less and further preferably 200° C. or less in consideration of exerting high molding process ability.

Both the melting point and the glass transition temperature of the polyimide resin can be measured by a differential scanning calorimeter.

In addition, in the polyimide resin of the present invention, the exothermic amount (hereinafter, also simply referred to as "exothermic amount of crystallization") of the crystallization exothermic peak observed in melting and then cooling of the polyimide resin at a cooling rate of 20° C./min with differential scanning calorimetric measurement is preferably 5.0 mJ/mg or more, more preferably 10.0 mJ/mg or more and further preferably 17.0 mJ/mg or more in consideration of enhancements in crystallinity, heat resistance, mechanical strength and chemical resistance. The upper limit of the exothermic amount of crystallization is not particularly limited, and is usually 45.0 mJ/mg or less.

Specifically, the melting point, the glass transition temperature and the exothermic amount of crystallization of the polyimide resin can be measured by the methods described in Examples.

The logarithmic viscosity of the polyimide resin of the present invention at 30° C. in a 5 mass % concentrated sulfuric acid solution is preferably 0.2 to 2.0 dL/g and more preferably 0.3 to 1.8 dL/g. When the logarithmic viscosity is 0.2 dL/g or more, a molded article obtained has sufficient mechanical strength, and when the logarithmic viscosity is 2.0 dL/g or less, molding processability and handleability are good. The logarithmic viscosity μ is obtained according to the following expression by measuring the elapsed times for flowing concentrated sulfuric acid and the polyimide resin solution at 30° C. with a Cannon-Fenske viscometer.

$$\mu = \ln(ts/t_0)/C$$

$t_0$: elapsed time for flowing concentrated sulfuric acid
ts: elapsed time for flowing polyimide resin solution
C: 0.5 (g/dL)

While the weight average molecular weight (Mw) of the polyimide resin of the present invention can be appropriately adjusted depending on the application, it is preferably 10,000 to 100,000, more preferably 12,000 to 80,000 and further preferably 13,000 to 60,000. When the Mw is 10,000 or more, mechanical strength is good, and when the Mw is 100,000 or less, molding processability is good. In addition, the number average molecular weight (Mn) of a polyamide resin is preferably 3,000 to 80,000, more preferably 4,000 to 50,000 and further preferably 5,000 to 30,000. The molecular weights (Mw, Mn) of the polyimide resin can be measured by a gel permeation chromatography (G-PC) method.

Furthermore, the polyimide resin of the present invention, after molded into a film having a thickness of 100 μm and heated at 200° C. for 72 hours, preferably has an Mw retention rate of 95% or more, more preferably 98% or more, and preferably has a Mn retention rate of 83% or more, more preferably 85% or more. When the Mw and Mn retention rates are in the above-described ranges, heat aging resistance is good.

The Mw retention rate may be more than 100%, and a preferred upper limit is 120%. When the Mw retention rate is more than 100%, it is considered that crosslinking occurs in the molecule. A preferred upper limit of the Mn retention rate is 100%.

The Mw and Mn retention rates can be calculated from the following expression.

{Molecular weight after heating at 200° C. for 72 hours/Molecular weight before heating}×100(%)

The form of the polyimide resin of the present invention is not particularly limited, and is preferably a powder form in consideration of handleability and the like. A polyimide resin powder, when subjected to the sieving test according to the method of JIS K0069, preferably passes through sieves with a nominal mesh opening of 500 μm for the JIS test in a proportion of 90 mass % or more, and more preferably passes through sieves with a nominal mesh opening of 250 μm in a proportion of 90 mass % or more. The polyimide resin powder has such a particle size and therefore has a large number of advantages of hardly causing the variation in processing during molding, being easily conveyed, being high in dispersibility when used as a filler, allowing a drying time to be reduced, and the like. In addition, the polyimide resin powder having the above particle size is preferable because of having high impregnating properties for a fiber material when used as a polyimide resin-fiber composite material mentioned later, in particular, when used as a continuous fiber composite material in a carbon fiber-reinforced plastic (CFRP) application or the like.

In addition, the polyimide resin powder preferably has a D10 of 8 to 100 μm, preferably has a D50 of 10 to 250 μm and preferably has a D90 of 20 to 500 μm in particle size measurement with a laser diffraction/light-scattering particle size distribution measuring instrument. Such a particle size range allows the advantages of good filtering properties, suppression of floating of particles, and the like, to be achieved in addition to the above advantages.

The polyimide resin powder having the above particle size is achieved by using, for example, a production method comprising a step of reacting a tetracarboxylic acid component with a diamine component in the presence of a solvent containing an alkylene glycol-based solvent represented by formula (I) mentioned later. Specifically, the sieving test and the particle size measurement with a laser diffraction/light-scattering particle size distribution measuring instrument, of the polyimide resin powder, can be performed by the methods described in Examples.

(Method for Producing Polyimide Resin)

The method for producing the polyimide resin of the present invention preferably includes the step of mixing a tetracarboxylic acid component and a diamine component, and then further mixing and reacting a compound having a chain aliphatic group having from 5 to 14 carbon atoms. The tetracarboxylic acid component contains a tetracarboxylic acid containing at least one aromatic ring and/or a derivative thereof, and the diamine component contains a diamine containing at least one alicyclic hydrocarbon structure and a chain aliphatic diamine. The compound having a chain aliphatic group having from 5 to 14 carbon atoms (hereinafter, also referred to as "compound for end group introduction") may be any compound as long as such a compound can cap a reaction end of a polyimide resin obtained by reacting a tetracarboxylic acid component and a diamine component, to introduce the chain aliphatic group having from 5 to 14 carbon atoms into the polyimide resin, and a monoamine mentioned later is preferred.

The tetracarboxylic acid containing at least one aromatic ring is preferably a compound having four carboxyl groups that are bonded directly to the aromatic ring, and may contain an alkyl group in the structure thereof. The tetracarboxylic acid preferably has from 6 to 26 carbon atoms. Preferred examples of the tetracarboxylic acid include pyromellitic acid, 2,3,5,6-toluenetetracarboxylic acid, 3,3',4,4'-benzophenonetetracarboxylic acid, 3,3',4,4'-biphenyltetracarboxylic acid and 1,4,5,8-naphthalenetetracarboxylic acid. Among these, pyromellitic acid is more preferred.

Examples of the derivative of the tetracarboxylic acid containing at least one aromatic ring include an anhydride and an alkyl ester compound of a tetracarboxylic acid containing at least one aromatic ring. The derivative of the tetracarboxylic acid preferably has from 6 to 38 carbon atoms. Examples of the anhydride of the tetracarboxylic acid include pyromellitic monoanhydride, pyromellitic dianhydride, 2,3,5,6-toluenetetracarboxylic dianhydride, 3,3',4,4'-diphenylsulfonetetracarboxylic dianhydride, 3,3',4,4'-benzophenonetetracarboxylic dianhydride, 3,3',4,4'-biphenyltetracarboxylic dianhydride and 1,4,5,8-naphthalenetetracarboxylic dianhydride. Examples of the alkyl ester compound of the tetracarboxylic acid include dimethyl pyromellitate, diethyl pyromellitate, dipropyl pyromellitate, diisopropyl pyromellitate, dimethyl 2,3,5,6-toluenetetracarboxylate, dimethyl diphenylsulfonetetracarboxylate, dimethyl 3,3',4,4'-benzophenonetetracarboxylate, dimethyl 3,3',4,4'-biphenyltetracarboxylate and dimethyl 1,4,5,8-naphthalenetetracarboxylate. The alkyl group in the alkyl ester compound of the tetracarboxylic acid preferably has from 1 to 3 carbon atoms.

The tetracarboxylic acid containing at least one aromatic ring and/or the derivative thereof may be used as a sole compound selected from the aforementioned compounds or may be used as a combination of two or more compounds.

The diamine containing at least one alicyclic hydrocarbon structure preferably has from 6 to 22 carbon atoms, and preferred examples thereof include 1,2-bis(aminomethyl)cyclohexane, 1,3-bis(aminomethyl)cyclohexane, 1,4-bis(aminomethyl)cyclohexane, 1,2-cyclohexanediamine, 1,3- cyclohexanediamine, 1,4-cyclohexanediamine, 4,4'-diaminodicyclohexylmethane, 4,4'-methylenebis(2-methylcyclohexylamine), carvone diamine, limonene diamine, isophorone diamine, norbornane diamine, bis(aminomethyl)tricyclo[5.2.1.0$^{2,6}$]decane, 3,3'-dimethyl-4,4'-diaminodicyclohexylmethane and 4,4'-diaminodicyclohexylpropane. These compounds may be used solely or may be used as a combination of two or more compounds selected therefrom. Among these, 1,3-bis(aminomethyl)cyclohexane is preferably used. A diamine containing an alicyclic hydrocarbon structure generally has conformational isomers, and the ratio of the cis isomer and the trans isomer is not particularly limited.

The chain aliphatic diamine may be in the form of either linear or branched chain, and has preferably from 5 to 16 carbon atoms, more preferably from 5 to 14 carbon atoms and further preferably from 5 to 12 carbon atoms. The linear moiety having from 5 to 16 carbon atoms may contain an ether bond in the course thereof. Preferred examples of the chain aliphatic diamine include 1,5-pentamethylenediamine, 2-methylpentane-1,5-diamine, 1,6-hexamethylenediamine, 1,7-heptamethylenediamine, 1,8-octamethylenediamine, 1,9-nonamethylenediamine, 1,10-decamethylenediamine, 1,11-undecamethylenediamine, 1,12-dodecamethylenediamine, 1,13-tridecamethylenediamine, 1,14-tetradecamethylenediamine, 1,16-hexadecamethylenediamine and 2,2'-(ethylenedioxy)bis(ethyleneamine).

The chain aliphatic diamine may be used as a sole compound or as a mixture of plural kinds thereof within the range of the present invention. Among these, a linear aliphatic diamine having from 6 to 12 carbon atoms can be preferably used, a linear aliphatic diamine having from 6 to 10 carbon atoms can be more preferably used, and at least one selected from the group consisting of 1,6-hexamethylenediamine, 1,8-octamethylenediamine and 1,10-decamethylenediamine can be particularly preferably used.

In the production of the polyimide resin of the present invention, the molar ratio of the charged amount of the diamine containing at least one alicyclic hydrocarbon structure with respect to the total amount of the diamine containing at least one alicyclic hydrocarbon structure and the chain aliphatic diamine is preferably 20 to 70 mol %. The molar ratio is preferably 25 mol % or more, more preferably 30 mol % or more and further preferably 32 mol % or more in consideration of molding processability, and is preferably 65 mol % or less, more preferably 60 mol % or less and further preferably 57 mol % or less in consideration of exerting high crystallinity.

The diamine component may contain a diamine containing at least one aromatic ring. The diamine containing at least one aromatic ring preferably has from 6 to 22 carbon atoms, and examples thereof include o-xylylenediamine, m-xylylenediamine, p-xylylenediamine, 1,2-diethynylbenzenediamine, 1,3-diethynylbenzenediamine, 1,4-diethynylbenzenediamine, 1,2-diaminobenzene, 1,3-diaminobenzene, 1,4-diaminobenzene, 4,4'-diaminodiphenyl ether, 3,4'-diaminodiphenyl ether, 4,4'-diaminodiphenylmethane, α,α'-bis(4-aminophenyl)-1,4-diisopropylbenzene, α,α'-bis(3-aminophenyl)-1,4-diisopropylbenzene, 2,2-bis(4-(4-aminophenoxy)phenyl)propane, 2,6-diaminonaphthalene and 1,5-diaminonaphthalene.

The molar ratio of the charged amount of the diamine containing at least one aromatic ring with respect to the total amount of the diamine containing at least one alicyclic hydrocarbon structure and the chain aliphatic diamine is preferably 25 mol % or less. The lower limit thereof is not particularly limited but needs to exceed 0 mol %.

The molar ratio is preferably 5 mol % or more, and more preferably 10 mol % or more, in consideration of enhancement of the heat resistance, and is preferably 20 mol % or less, and more preferably 15 mol % or less, in consideration of maintenance of the crystallinity.

In addition, the molar ratio is preferably 12 mol % or less, more preferably 10 mol % or less, further preferably 5 mol % or less and still more preferably 0 mol % in consideration of a decrease in coloration of the polyimide resin.

In the production of the polyimide resin, the charged amount ratio of the tetracarboxylic acid component and the diamine component is preferably from 0.9 to 1.1 mol of the diamine component per 1 mol of the tetracarboxylic acid component.

The compound having a chain aliphatic group having from 5 to 14 carbon atoms (compound for end group introduction) is preferably at least one selected from the group consisting of a monoamine having a chain aliphatic group having from 5 to 14 carbon atoms and a dicarboxylic acid, and more preferably such a monoamine. The monoamine is preferably a monoamine having a saturated chain aliphatic group, and more preferably a monoamine having a saturated linear aliphatic group.

The chain aliphatic group preferably has 6 or more carbon atoms, more preferably 7 or more carbon atoms and further preferably 8 or more carbon atoms, and preferably has 12 or less carbon atoms, more preferably 10 or less carbon atoms and further preferably 9 or less carbon atoms in consideration of achievement of the effect of the present invention. A compound for end group introduction containing a chain aliphatic group having 4 or less carbon atoms is not preferable because of being easily volatilized in production of the polyimide resin. On the other hand, a compound for end group introduction containing a chain aliphatic group having more than 14 carbon atoms has a reduced solvent solubility and is deteriorated in reactivity.

Specific examples of the monoamine include n-pentylamine, n-hexylamine, n-heptylamine, n-octylamine, n-nonylamine, n-decylamine, n-undecylamine, laurylamine, n-tridecylamine, n-tetradecylamine, isopentylamine, neopentylamine, 2-methylpentylamine, 2-methylhexylamine, 2-ethylpentylamine, 3-ethylpentylamine, isooctylamine, 2-ethylhexylamine, 3-ethylhexylamine, isononylamine, 2-ethyloctylamine, isodecylamine, isododecylamine, isotridecylamine, isotetradecylamine. Such a monoamine may be used singly or in combinations of two or more.

The monoamine is particularly preferably at least one selected from the group consisting of n-octylamine, isooctylamine, 2-ethylhexylamine, n-nonylamine, isononylamine, n-decylamine and isodecylamine, further preferably at least one selected from the group consisting of n-octylamine, isooctylamine, 2-ethylhexylamine, n-nonylamine and isononylamine, and most preferably at least one selected from the group consisting of n-octylamine, isooctylamine and 2-ethylhexylamine.

The amount of the compound having a chain aliphatic group having from 5 to 14 carbon atoms, to be used, may be any amount as long as the aforementioned desired amount of the chain aliphatic group having from 5 to 14 carbon atoms can be introduced into the polyimide resin, and the amount is preferably 0.0001 to 0.1 mol, more preferably 0.001 to 0.06 mol and further preferably 0.002 to 0.035 mol per 1 mol of the tetracarboxylic acid and/or the derivative thereof. When the amount is in the aforementioned range, a polyimide resin excellent in heat aging resistance can be obtained.

As a polymerization method for producing the polyimide resin, a known polymerization method for producing a polyimide resin may be applied, and examples thereof include, for example, solution polymerization, melt polymerization, solid phase polymerization, suspension polymerization and the like while not particularly limited. Among these, suspension polymerization under a high temperature condition using an organic solvent is preferred. On performing suspension polymerization under a high temperature condition, the polymerization is preferably performed at 150° C. or more, and more preferably at from 180 to 250° C. The polymerization time may vary depending on the monomers used, and is preferably approximately from 0.1 to 6 hours.

The method for producing the polyimide resin preferably includes the step of reacting the tetracarboxylic acid component with the diamine component in the presence of a solvent containing an alkylene glycol-based solvent represented by the following formula (I). In this way, the polyimide resin may be obtained in a powder form. The production method is preferable in that a polyimide resin powder can be easily obtained which, when subjected to the sieving test according to the method of JIS K0069, passes through sieves with a nominal mesh opening of 500 μm for the JIS test in a proportion of 90 mass % or more, and a polyimide resin powder can be easily obtained which has a D10 of 8 to 100 μm, a D50 of 12 to 250 μm and a D90 of 20 to 500 μm in particle size measurement with a laser diffraction/light-scattering particle size distribution measuring instrument.

$$Ra_1-O-(Ra_2-O-)_n H \quad (I)$$

wherein $Ra_1$ represents a hydrogen atom or an alkyl group having from 1 to 4 carbon atoms; $Ra_2$ represents a linear alkylene group having from 2 to 6 carbon atoms; and n represents an integer of 1-3.

In order to obtain a homogeneous powder polyimide resin, it is considered to be desirable that the solvent in a one-pot reaction possess two properties of (1) homogeneously dissolving a polyamic acid or homogeneously dispersing a nylon salt, and (2) not dissolving and swelling the polyimide resin at all. A solvent containing the alkylene glycol-based solvent represented by the formula (I) generally satisfies the two properties.

The alkylene glycol-based solvent has a boiling point of preferably 140° C. or more, more preferably 160° C. or more, and further preferably 180° C. or more, in consideration of feasible polymerization reaction under high temperature conditions at normal pressure.

In the formula (I), $Ra_1$ represents a hydrogen atom or an alkyl group having from 1 to 4 carbon atoms and is preferably an alkyl group having from 1 to 4 carbon atoms, and more preferably a methyl group or an ethyl group.

In the formula (I), $Ra_2$ represents a linear alkylene group having from 2 to 6 carbon atoms and is preferably a linear alkylene group having 2 or 3 carbon atoms, and more preferably an ethylene group.

In the formula (I), n represents an integer of 1-3 and is preferably 2 or 3.

Specific examples of the alkylene glycol-based solvent include ethylene glycol monomethyl ether, diethylene glycol monomethyl ether (also known as 2-(2-methoxyethoxy)ethanol), triethylene glycol monomethyl ether, ethylene glycol monoethyl ether, diethylene glycol monoethyl ether (also known as 2-(2-ethoxyethoxy)ethanol), ethylene glycol monoisopropyl ether, diethylene glycol monoisopropyl ether, triethylene glycol monoisopropyl ether, ethylene glycol monobutyl ether, diethylene glycol monobutyl ether, triethylene glycol monobutyl ether, ethylene glycol monoisobutyl ether, diethylene glycol monoisobutyl ether, ethylene glycol monoisobutyl ether, ethylene glycol, and 1,3-propanediol. These solvents may each be used alone, or two or more solvents selected from them may be used in combination. Among these solvents, 2-(2-methoxyethoxy)ethanol, triethylene glycol monomethyl ether, 2-(2-ethoxyethoxy)ethanol, and 1,3-propanediol are preferred, and 2-(2-methoxyethoxy)ethanol and 2-(2-ethoxyethoxy)ethanol are more preferred.

The content of the alkylene glycol-based solvent in the solvent is preferably 30 mass % or more, more preferably 50 mass % or more, further preferably 75 mass % or more, and particularly preferably 95 mass % or more. The solvent may consist of the alkylene glycol-based solvent alone.

When the solvent contains the alkylene glycol-based solvent and an additional solvent, specific examples of the "additional solvent" include water, benzene, toluene, xylene, acetone, hexane, heptane, chlorobenzene, methanol, ethanol, n-propanol, isopropanol, butanol, pentanol, hexanol, heptanol, octanol, N-methyl-2-pyrrolidone, N,N-dimethylacetamide, N,N-diethylacetamide, N,N-dimethylformamide, N,N-diethylformamide, N-methylcaprolactam, hexamethylphosphoramide, tetramethylene sulfone, dimethylsulfoxide, o-cresol, m-cresol, p-cresol, phenol, p-chlorophenol, 2-chloro-4-hydroxytoluene, triglyme, tetraglyme, dioxane, γ-butyrolactone, dioxolane, cyclohexanone, cyclopentanone, dichloromethane, chloroform, 1,2-dichloroethane, 1,1,2-trichloroethane, dibromomethane, tribromomethane, 1,2-dibromoethane, and 1,1,2-tribromoethane. These solvents may each be used alone, or two or more solvents selected from them may be used in combination.

Preferred examples of the method for producing the polyimide resin include a method which involves separately preparing (a) a solution containing the tetracarboxylic acid component in the solvent containing the alkylene glycol-based solvent and (b) a solution containing the diamine component in the solvent containing the alkylene glycol-based solvent, then adding the solution (b) to the solution (a) or adding the solution (a) to the solution (b), thereby preparing (c) a solution containing a polyamic acid, and subsequently imidizing the polyamic acid by the heating of the solution (c), thereby synthesizing a polyimide resin.

While the reaction of the tetracarboxylic acid component with the diamine component can be performed either under normal pressure or under pressure, the reaction is preferably performed under normal pressure because no pressure resistant container is required under normal pressure.

With respect to the compound for end group introduction, it is preferable to mix the solution (a) and the solution (b), mix the compound for end group introduction with the mixed solution to prepare the solution (c) containing a polyamic acid, and subsequently heat the solution (c), and it is more preferable to add the compound for end group introduction after completion of addition of the solution (b) to the solution (a), to prepare the solution (c) containing a polyamic acid, and subsequently heat the solution (c).

In the method for producing the polyimide resin, preferably, the tetracarboxylic acid component contains a tetracarboxylic dianhydride; the step of reacting the tetracarboxylic acid component with the diamine component includes: step (i) of adding (b) a solution containing the diamine component and the alkylene glycol-based solvent to (a) a solution containing the tetracarboxylic acid component and the alkylene glycol-based solvent, thereby preparing (c) a solution containing a polyamic acid; and step (ii) imidizing the polyamic acid by the heating of the solution (c), thereby providing a polyimide resin; and in the step (i), the solution (b) is added to the solution (a) such that the amount of the diamine component added per unit time with respect to 1 mol of the tetracarboxylic acid component is 0.1 mol/min or less, in consideration of reduction in the amount of by-products in the polyimide resin.

The polyimide resin of the present invention may also be mixed, if necessary, with an arbitrary component such as a delusterant, a crystal nucleating agent, a plasticizer, an antistatic agent, an anti-coloring agent, an anti-gelling agent, and a resin-modifying agent, without impairing its characteristics.

The polyimide resin of the present invention may be a resin composition with which at least one additive selected from the group consisting of a filler, a flame retardant, a colorant, a slidability-improving agent, an antioxidant and a conducting agent is mixed, in consideration of use of the original physical properties thereof and also imparting desired performances.

The filler is preferably an inorganic filler in consideration of heat resistance and mechanical strength. The shape of the filler is not particularly limited, and any of particulate, plate-like and fibrous fillers can be used. Examples of the particulate or plate-like inorganic filler among the inorganic fillers include silica, alumina, kaolinite, wollastonite, mica, talc, clay, sericite, magnesium carbonate, magnesium sulfate, calcium oxide, silicon carbide, antimony trisulfide, tin sulfide, copper sulfide, iron sulfide, bismuth sulfide, zinc sulfide, a metal powder, a glass powder, a glass flake, and glass beads. Examples of the fibrous inorganic filler include glass fiber, carbon fiber, metal fiber, graphite fiber, silica fiber, silica-alumina fiber, alumina fiber, zirconia fiber, boron nitride fiber, silicon nitride fiber, boron fiber, potassium titanate whisker, aluminum borate whisker, magnesium-based whisker, and silicon-based whisker. Examples of the carbon fiber include polyacrylonitrile-based carbon fiber and pitch-based carbon fiber. Such inorganic fillers may also be surface-treated.

Examples of the flame retardant include a halogen-based flame retardant, a phosphorus-based flame retardant, a metal oxide-based flame retardant, a metal hydroxide-based flame retardant, a metal salt-based flame retardant, a nitrogen-based flame retardant, a silicone-based flame retardant, and a boron compound-based flame retardant.

A pigment, a dye, and the like can be appropriately selected and used as the colorant depending on the intended application and coloration. A pigment and a dye may be used in combination.

Examples of the slidability-improving agent include solid lubricants such as molybdenum disulfide and metal soap; liquid lubricants such as mineral oil, synthetic oil and wax; and lubricating polymers such as a fluororesin, polyolefin and spherical phenol.

Examples of the antioxidant include a phenol-based antioxidant, a sulfur-based antioxidant, a phosphorus-based antioxidant, a copper-based antioxidant, and an amine-based antioxidant. Examples of the conducting agent include a carbon-based conducting agent, a metal-based conducting agent, a metal oxide-based conducting agent, and a surfactant.

Such an additive can be used singly or in combinations of two or more.

The amount of the additive to be mixed in the polyimide resin composition is not particularly limited, and is preferably 0.0001 to 80 mass %, more preferably 0.001 to 70 mass %, and further preferably 0.01 to 65 mass % in consideration of maintaining physical properties of the polyimide resin and also exerting the effect of the additive.

The polyimide resin composition may also contain a resin other than the polyimide resin of the present invention. The polyimide resin of the present invention can be used in combination with other resin and thus used as a polymer alloy, thereby allowing the functions depending on various applications to be imparted. Such other resin is preferably a high heat resistant thermoplastic resin, and examples thereof include a polyamide resin, a polyester resin, a polyimide resin other than that of the present invention, a polycarbonate resin, a polyetherimide resin, a polyamideimide resin, a polyphenylene ether imide resin, a polyphenylene sulfide resin, a polysulfone resin, a polyethersulfone resin, a polyallylate resin, a liquid crystal polymer, a polyether ether ketone resin, and a polybenzimidazole resin. Among these, one or more selected from the group consisting of a polyetherimide resin, a polyphenylene sulfide resin and a polyether ether ketone resin are preferable and a polyether ether ketone resin is more preferable in consideration of heat resistance, strength and solvent resistance.

When the polyimide resin of the present invention is used in combination with other resin, the rate of such other resin to be mixed is not particularly limited, and the ratio of the polyimide resin of the present invention and other resin to be mixed is preferably 1/99 to 99/1, more preferably 5/95 to 95/5, and further preferably 10/90 to 90/10 in mass ratio in consideration of exerting characteristics of the polyimide resin of the present invention. Even when the rate of the polyimide resin of the present invention to be mixed is lower than that of other resin, the polyimide resin exerts, for example, the effect of serving as a nucleating agent for an increase in the exothermic amount of crystallization of a resin composition obtained.

The polyimide resin of the present invention, and the polyimide resin composition can be used for preparation of a molded article and a polyimide resin-fiber composite material mentioned later. The polyimide resin powder described above also has a sharp particle size distribution, and therefore can be utilized for a heat resistance-improving filler, a slidability-improving filler, a resin paste, a resin material for impregnation of fiber, a resin material for impregnation of fabric, a resin material for a 3D printer, a resin material for compression molding, and the like.

[Molded Article]

The molded article of the present invention contains the polyimide resin of the present invention. Since the polyimide resin of the present invention is excellent in molding processability, the molded article can be easily produced by heat-molding the polyimide resin and the polyimide resin composition comprising the resin. Examples of the heat molding method include injection molding, extrusion molding, blow molding, heat press molding, vacuum molding, pneumatic molding, laser molding, welding and heat adhesion, and the polyimide resin of the present invention may be molded by any molding method that includes a heat melting step.

The method for producing a molded article according to the present invention preferably comprises the step of heat-molding the polyimide resin of the present invention at from 290 to 400° C. Examples of specific procedures include the following method.

First, various arbitrary components are, if necessary, added to the polyimide resin and dry blended, and thereafter the resulting mixture is introduced into an extruder, and melt-kneaded and extruded preferably at from 290 to 400° C., thereby producing a pellet. Alternatively, the polyimide resin may be introduced into an extruder and molten preferably at from 290 to 400° C., and various arbitrary components may be introduced thereto, melt-kneaded with the polyimide resin in the extruder, and extruded, thereby producing the pellet.

The pellets may be dried, then introduced in various kinds of molding machines, and heat-molded preferably at from 290 to 400° C., thereby producing a molded article having a desired shape.

Since the polyimide resin of the present invention and the polyimide resin composition containing the polyimide resin may be heat-molded by extrusion molding or the like at a relatively low temperature of from 290 to 400° C., the polyimide resin of the present invention and the polyimide resin composition comprising the polyimide resin are excellent in molding processability and may be easily produced into a molded product having a desired shape. The temperature of the heat molding is preferably from 300 to 380° C., more preferably from 310 to 370° C.

Examples of the shape of the molded article of the present invention include, but are not particularly limited to, a film, a sheet, a strand, pellets, fibers, a round bar, a rectangular bar, a sphere, a pipe, a tube, and a seamless belt.

The polyimide resin of the present invention and the polyimide resin composition comprising the polyimide resin are particularly excellent in molding processability, and therefore are preferably used for preparing a molded article at least partially having a thin portion having a thickness of 1000 µm or less. Examples include a film and a sheet each having a uniform thickness of 1000 µm or less, and an injection-molded article at least partially having a thin portion having a thickness of 1000 µm or less. The thickness is preferably 1000 µm or less and more preferably 800 µm or less.

The application of the molded article of the present invention is also not limited, and representative examples include a film, fiber, a heat-resistant adhesive, a color filter, a solar cell substrate, a wafer carrier, an IC tray, a seal ring, a bearing for automobiles and a bearing for copiers, as well as a fixing belt and an intermediate transfer belt for various electrophotographic image formation apparatuses such as a copier, a printer, a facsimile apparatus and a composite apparatus thereof, or a transfer roll, a printed circuit board, a copper-clad laminate, an insulating film, a heat-resistant protection film, a reflective material for lighting, a laminate material of a septum material for vehicles and aircrafts, a separator for fuel cells, a TAB spacer, a heat-resistant sheet, a flameproof sheet, and various switches. Examples of the application where heat aging resistance is required include a member for use in automobiles, such as a gear, a tube and a pipe; a sliding member for use in a copier and the like; as well as an industrial piping, an electronic member and an electric wire, and a covering material for use in an electronic member, a sensor member, a piping, an electric wire and the like.

The film as the molded article of the present invention may be either a non-stretched film or a stretched film, and is preferably a stretched film in consideration of enhancement of mechanical strength and heat resistance of the film.

When the molded article of the present invention is a film, a known film production method can be applied for production of the film. Examples of the method for producing a non-stretched film include a method comprising drying the pellet of the polyimide resin prepared by the aforementioned method, thereafter introducing the pellet into an extruder and melting it, discharging the polyimide resin in the form of a film according to a common T-die method, a cylindrical die method (inflation method) or the like, and then cooling and solidifying such a film by a cooling roll or the like to provide a film. A uniaxial or biaxial screw extruder and the like can be used as the extruder.

Examples of other method for producing a non-stretched film include a method comprising providing a polyimide resin solution containing the polyimide resin of the present invention and an organic solvent or a polyimide resin composition comprising the polyimide resin and various additives described above in the form of a film by coating or molding, and thereafter removing the organic solvent.

Examples of the method for producing a stretched film include a method containing stretching the non-stretched film used as a raw material roll film. The thickness of the raw material roll film is not particularly limited, can be appropriately selected depending on the stretching ratio, the stretching temperature, the theoretical thickness of a stretched film to be produced, and the like, and is usually in the range from 50 to 2000 µm.

In production of a stretched film, stretching may be uniaxial stretching or biaxial stretching and can be appropriately selected depending on the application of the film and physical properties to be demanded. As the biaxial stretching method, a simultaneous biaxial stretching method or a sequential biaxial stretching method can be used. Biaxial stretching is preferable in consideration of reduction in anisotropy between the MD direction and the TD direction of the film.

In production of a stretched film, first, a raw material roll film to be used is preferably preheated. The preheating temperature is preferably from Tg of the polyimide resin to Tg+5° C. or more and more preferably from Tg of the polyimide resin to Tg+10° C. or more in order to impart a sufficient stretching ratio with neither breaking nor defects being caused, and is preferably from Tg of the polyimide resin to Tg+70° C. or less and more preferably from Tg of the polyimide resin to Tg+50° C. or less in order to allow physical properties to be enhanced by stretching. The preheating time is preferably 10 seconds or more, more preferably 20 seconds or more, and further preferably 30 seconds or more in consideration of uniform heating of the raw material roll film to the set temperature, and is preferably 90 seconds or less and more preferably 60 seconds or less in consideration of productivity.

While the preheating is performed to uniformly heat the raw material roll film to the set temperature, the film is stretched in the MD direction or the TD direction when uniaxially stretched, and the film is stretched in the MD direction and the TD direction when biaxially stretched. The stretching ratio is preferably 1.1 times or more and more preferably 1.2 times or more, and is preferably 4.0 times or less, more preferably 3.5 times or less, further preferably 3.0 times or less and still more preferably 2.5 times or less, in both the MD direction and the TD direction. When the stretching ratio is 1.1 times or more, stretch orientation is sufficiently achieved and the effect of enhancement of physical properties such as mechanical strength and heat resistance is easily exerted. When the stretching ratio is 4.0 times or less, breaking, defects and the variation in orientation of the film due to stretching can be prevented from being caused, and a film excellent in appearance characteristics can be obtained.

While the product of the stretching ratios of the stretched film in the MD direction and in the TD direction differs depending on the thickness of a raw material roll film to be used, the product is preferably 1.5 to 16 times, more preferably 1.5 to 12.25 times, further preferably 1.5 to 9.0 times, and still more preferably 1.5 to 6.25 times (under the assumption that the ratio in the direction in which no stretching is performed is 1 time in uniaxial stretching) in consideration of physical properties and appearance characteristics of a film obtained. When any anisotropy is observed in the MD direction and the TD direction in stretching at the same stretching ratios, stretching can also be performed in the MD direction and the TD direction at different stretching ratios to reduce anisotropy.

The stretching temperature is preferably from Tg of the polyimide resin to Tg+10° C. or more and more preferably from Tg of the polyimide resin to Tg+20° C. or more, and preferably from Tg of the polyimide resin to Tg+70° C. or less, more preferably from Tg of the polyimide resin to Tg+60° C. or less and further preferably from Tg of the polyimide resin to Tg+50° C. or less. When the stretching temperature is from Tg of the polyimide resin to Tg+10° C. or more, stretching failures such as breaking and defects can be decreased, and the haze of the stretched film can be reduced. When the stretching temperature is from Tg of the polyimide resin to Tg+70° C. or less, physical properties can be sufficiently allowed to be enhanced by stretching.

The stretching rate is preferably 10%/min or more and more preferably 50%/min or more in consideration of sufficient enhancement of physical properties of a film obtained. The upper limit of the stretching rate is not particularly limited as long as defects such as breaking are not caused, and the upper limit is usually 10000%/min or less.

A known uniaxial or biaxial stretching apparatus can be used for stretching.

After the stretching is performed, heat fixation of the film is preferably performed. The heat fixation refers to a treatment where a film stretched is heated and cooled under strain or under limited shrinkage. The heat fixation can be performed, thereby suppressing the change in dimension (thermal shrinkage) of the film in reheating, with stretch orientation of the film being maintained.

The heating temperature in the heat fixation may be a temperature equal to or more than Tg of the polyimide resin and equal to or less than the melting point thereof, and is preferably from Tg of the polyimide resin to Tg+10° C. or more and more preferably from Tg of the polyimide resin to Tg+20° C. or more in consideration of suppression of the change in dimension of the film in reheating. In addition, the heating temperature is preferably from the melting point of the polyimide resin to the melting point −30° C. or less and more preferably from the melting point of the polyimide resin to the melting point −50° C. or less in consideration of maintaining stretch orientation of the film. The heating time is preferably 0.5 to 1000 minutes and more preferably 1 to 500 minutes in consideration of suppression of the change in dimension of the film in reheating.

The stretched film after the heat fixation is preferably less changed in terms of dimension in reheating. Specifically, the coefficient of linear thermal expansion (CTE) measured at the temperature range from 100 to 150° C. is preferably 50 ppm or less, more preferably 40 ppm or less and further preferably 30 ppm or less. The lower limit of the coefficient of linear thermal expansion is preferably lower, and the coefficient of linear thermal expansion measured at the temperature range from 100 to 150° C. is preferably 0 ppm or more in consideration of properties of the polyimide resin film and in consideration of avoidance of deterioration in productivity due to prolonged heat fixation. Specifically, the coefficient of linear thermal expansion can be measured by the method described in Examples.

(Polyimide Resin-Fiber Composite Material)

The polyimide resin of the present invention can also be used for impregnation of the fiber material to provide a polyimide resin-fiber composite material (hereinafter, simply also referred to as "composite material").

Examples of the fiber material used in the composite material include: inorganic fibers, such as glass fiber, carbon fiber, alumina fiber, boron fiber, ceramic fiber, and metal fiber (steal fiber, etc.); and synthetic fibers, such as aramid fiber, polyoxymethylene fiber, aromatic polyamide fiber, poly-p-phenylene benzobisoxazole fiber, ultra-high molecular weight polyethylene fiber, and aromatic polyimide fiber. Among these, carbon fiber is preferably used because of having excellent features, i.e., high strength and a high modulus of elasticity in spite of its light weight. Polyacrylonitrile-based carbon fiber or pitch-based carbon fiber is preferably used as the carbon fiber.

The fiber material may be in various forms, for example, monofilaments or multifilaments simply arranged in one direction or intercrossed, a fabric, such as a knit fabric, a non-woven fabric, or a mat. Among these, a monofilament, fabric, non-woven fabric, or mat form is preferred. Prepreg in which these are mounted or laminated and impregnated with a binder or the like is also preferably used.

The average fiber diameter of the fiber material is preferably from 1 to 100 µm, more preferably from 3 to 50 µm, further preferably from 4 to 20 µm, and particularly preferably from 5 to 10 µm. When the average fiber diameter falls within this range, processing is easy and the resulting molded article is excellent in modulus of elasticity and strength. The average fiber diameter may be measured by observation under a scanning electron microscope (SEM) or the like. 50 or more fibers are selected at random, and their lengths are measured. A number-average fiber diameter may be calculated.

The fineness of the fiber material is preferably from 20 to 3,000 tex, and more preferably from 50 to 2,000 tex. When the fineness falls within this range, processing is easy and the resulting molded article is excellent in modulus of elasticity and strength. The fineness may be determined in terms of weight per 1,000 m by determining the weights of long fibers having an arbitrary length. Carbon fiber generally having approximately from 500 to 30,000 fiber material is preferably used.

The fiber length of the fiber material present in the composite material is preferably 1 cm or more, more preferably 1.5 cm or more, further preferably 2 cm or more, and particularly preferably 3 cm or more, in terms of average fiber length. The upper limit of the average fiber length differs depending on use application and is preferably 500 cm or less, more preferably 300 cm or less, and further preferably 100 cm or less.

The method for measuring the average fiber length in the composite material is not particularly limited, and the average fiber length may be determined, for example, by placing the composite material in hexafluoroisopropanol (HFIP) or concentrated sulfuric acid and measuring the lengths of fibers remaining after the dissolution of the polyimide resin. The lengths of the fibers may be measured by visual observation or in some cases, observation under an optical microscope, a scanning electron microscope (SEM) or the like. 100 fibers are selected at random, and their lengths are measured. A number-average fiber length may be calculated.

The average fiber length of a raw material before use of the fiber material used is not particularly limited and is preferably in the range of from 1 to 10,000 m, more preferably on the order of from 100 to 7,000 m, and further preferably on the order of from 1,000 to 5,000 m, in consideration of improvement in molding processability.

It is not intended to exclude combination use of a chopped fiber (D) of the fiber material in the composite material. In the case of using the fiber material in combination with a chopped fiber (D), the average fiber diameter of the chopped fiber (D) is preferably shorter than that of the fiber material.

A fiber material having, on its surface, a functional group having affinity for or reactivity with the polyimide resin is preferred for improving wettability and interface adherence with the polyimide resin.

Preferred examples of the fiber material having a functional group having affinity for or reactivity with the polyimide resin include a fiber material surface-treated with a surface treatment agent or a sizing agent or the like.

Examples of the surface treatment agent include surface treatment agents consisting of functional compounds, such as epoxy compounds, acrylic compounds, isocyanate compounds, silane compounds, and titanate compounds. The surface treatment agent is, for example, a silane-based coupling agent or a titanate-based coupling agent, and is preferably a silane-based coupling agent.

Examples of the silane-based coupling agent include trialkoxy- or triallyloxy-silane compounds, such as aminopropyltriethoxysilane, phenylaminopropyltrimethoxysilane, glycidylpropyltriethoxysilane, methacryloxypropyltrimethoxysilane, and vinyltriethoxysilane; ureidosilane, sulfide silane, vinylsilane, and imidazolesilane.

The sizing agent is an epoxy resin, such as bisphenol A-type epoxy resin, or an epoxy acrylate resin having an acryl group or a methacryl group in one molecule. Preferred examples thereof include vinyl ester resins, such as bisphenol A-type vinyl ester resins, novolac-type vinyl ester resins, and brominated vinyl ester resins. Alternatively, the sizing agent may be an urethane-modified resin of an epoxy resin or a vinyl ester resin.

The polyimide resin is overlaid with the fiber material. Subsequently, the whole amount or at least a portion of the polyimide resin is melted by applying heat and pressure so that the fiber material layer is impregnated with the polyimide resin. This impregnated product is consolidated (compacted) into a composite material by applying heat and pressure.

The polyimide resin may be prepared, in any form, such as a film, fibrous, powder, or pellet form, into a composite with the fiber material and is preferably in a film, fibrous, or powder form, in consideration of moldability, impregnating properties and the like.

A known method may be adopted for preparing the polyimide resin in a film or fibrous form. For example, the polyimide resin in this form is produced by a method, for example, fiber production by melt spinning from polyimide resin pellets, continuous film formation by the extrusion of the resin from an extruder, or film formation with a heat pressing machine.

When the polyimide resin is in a film or fibrous form, the step of impregnating the fiber material with the polyimide resin is preferably performed by continuously applying pressure with plural rolls in a heated atmosphere. The continuous application of pressure is capable of pushing air contained in the fiber material out of the composite material or a molded article obtained by molding this composite material, and is capable of decreasing voids in the composite material or the molded article obtained by molding this composite material.

The material of the roll is not particularly limited, and a roll with its surface coated with a fluorine resin is preferably used for preventing the adhesion of the polyimide resin to the roll during the application of heat and pressure.

When the polyimide resin is in a powder form, the powder of the polyimide resin may be dispersed in the surface of the fiber material and then melted by applying pressure with a roll in a heated atmosphere or by laser irradiation so that the fiber material is impregnated with the polyimide resin.

The application of heat and pressure may be performed to two or more superimposed layers of the film or fiber of the polyimide resin overlaid or laminated with the fiber material. In the case of such two or more superimposed layers, for example, it is desirable to superimpose at least two, and preferably five or more polyimide resin film/fiber material laminates such that the polyimide resin layers are positioned on both outermost sides, respectively, and to apply heat and pressure to the superimposed laminates.

The temperature for impregnating and integrating the fiber material layer with the polyimide resin by applying heat and pressure needs to be equal to or higher than the temperature at which the polyimide resin is softened and melted. This temperature differs depending on the type or molecular weight of the polyimide resin and is preferably from 300 to 400° C., and more preferably from 300 to 380° C. The application of heat and pressure in such a temperature range tends to further improve the impregnation of the fiber material with the polyimide resin and to improve the physical properties of the composite material or the molded article obtained by molding this composite material.

The press pressure for the application of pressure is preferably 0.1 MPa or more. The application of heat and pressure is preferably performed under reduced pressure, and in particular, in vacuum. The application of heat and pressure under such conditions is preferred because bubbles are less likely to remain in the resulting composite material.

The composite material thus produced may be solid, semisolid, or viscous and is not particularly limited by its form. Generally, the composite material of the present invention is solid or semisolid. Preferably, the composite material is capable of being taken up in a roll form and stored. Since the polyimide resin is thermoplastic, the composite material may be further thermally processed into a molded article by various kinds of molding methods.

In the composite material, the polyimide resin/fiber material area ratio at the cross section is preferably from 20/80 to 80/20. The area ratio at the cross section is more preferably from 30/70 to 70/30, and further preferably from 40/60 to 60/40. When the fiber material is oriented in one direction, the cross section refers to a cross section perpendicular to the longitudinal direction of the fiber material. When the fiber material is oriented in plural directions, the cross section is defined as a surface perpendicular to the longitudinal direction of the fiber material oriented in one direction arbitrarily selected from the plural directions. When the fiber material is not oriented, the cross section is defined as arbitrary one direction of the composite material. The polyimide resin/fiber material area ratio may be determined by observing the cross section under a scanning electron microscope (SEM).

The composite material obtained by the aforementioned method preferably has both surfaces respectively constituted by the polyimide resin layers comprising the polyimide resin of the present invention.

Since the composite material described above consists of a thermoplastic resin material, this is used as a material for molding, either as it is or after being cut into a desired shape or size, and this may be preferably heated, subsequently molded, preferably, in a heated molding pattern, and removed from the pattern, thereby providing various kinds of molded articles. The molding is not limited to the method using a molding pattern and may be performed with, for example, a roll. The composite material may be preferably heated and subsequently molded by applying pressure, preferably, with a heated roll.

The method for processing the composite material described above into a molded article is not particularly limited, and a known technique may be applied. A compression molding method, a vacuum molding method, a vacuum compression molding method, a pressure molding method or the like may be used.

The molded article obtained by molding the composite material may be further heat-treated. The heat treatment of the molded article is capable of reducing curvature and further improving dimensional stability. The heat treatment temperature is preferably from 150 to 250° C.

EXAMPLES

The present invention will be described in more detail with reference to examples below, but the present invention is not limited thereto. Various measurements and evaluations in each Production Example, Example, and Reference Example were carried out in the following manners.

<Logarithmic Viscosity $\mu$>

The logarithmic viscosity $\mu$ of the polyimide resin was measured in such a manner that the resulting polyimide resin was dried at from 190 to 200° C. for 2 hours, and 0.100 g of the polyimide resin was dissolved in 20 mL of concentrated sulfuric acid (96%, produced by Kanto Chemical Co., Inc.), and measured at 30° C. with a Cannon-Fenske viscometer. The logarithmic viscosity $\mu$ was obtained according to the following expression.

$$\mu = \ln(t_s/t_0)/C$$

$t_0$: elapsed time for flowing concentrated sulfuric acid
$t_s$: elapsed time for flowing polyimide resin solution
C: 0.5 g/dL <Melting Point, Glass Transition Temperature, Crystallization Temperature, and Exothermic Amount of Crystallization>

The melting point (Tm), the glass transition temperature (Tg), the crystallization temperature (Tc) and the exothermic amount of crystallization of the polyimide resin were measured with a differential scanning calorimeter ("DSC-6220", produced by SII Nanotechnology, Inc.). The polyimide resin was subjected to the following thermal history in a nitrogen atmosphere. The condition of the thermal history included the first heating (heating rate: 10° C./min), then cooling (cooling rate: 20° C./min), and then second heating (heating rate: 10° C./min).

The melting point was determined by reading the peak top value of the endothermic peak observed in the second heating. The glass transition temperature was determined by reading the value observed in the second heating.

The crystallization temperature was determined by reading the peak top value of the exothermic peak observed in cooling.

The exothermic amount of crystallization (mJ/mg) was calculated from the area of the crystallization exothermic peak observed in cooling.

<Crystallization Half-Time>

The crystallization half-time of the polyimide resin was measured with a differential scanning calorimeter ("DSC-6220", produced by SII Nanotechnology, Inc.).

A polyimide resin having a crystallization half-time of 20 seconds or less was measured under such conditions that in a nitrogen atmosphere, the polyimide resin was held at the melting point +20° C. for 10 minutes for melting the polyimide resin completely, and then quenched at a cooling rate of 70° C./min, during which the time required from the appearance of the crystallization heating peak observed to the peak top thereof was calculated for determining the crystallization half-time.

In Table 2, a crystallization half-time of less than 20 seconds in Examples and Comparative Examples was designated as "20>".

<Infrared Spectroscopy (IR Measurement)>

The IR measurement of the polyimide resin was performed with "JIR-WINSPEC 50", produced by JEOL, Ltd.

<Sieving Test>

The polyimide resin powder was subjected to the sieving test according to JIS K0069 using sieves with a nominal mesh opening of 500 µm and a nominal mesh opening of 250 µm for the JIS test, to confirm the particle size.

<Laser Diffraction Particle Size Distribution Measurement>

A laser diffraction particle size distribution measuring instrument "LMS-2000e" produced by Malvern Instruments Ltd. was used for laser diffraction particle size distribution measurement of the polyimide resin powder. The measurement was performed with water as a dispersion medium in a condition where the polyimide resin powder was sufficiently dispersed under an ultrasonic condition. The measurement range was from 0.02 to 2000 µm.

<Molecular Weight Measurement>

The molecular weights (Mw, Mn) of the polyimide resin were measured with a gel permeation chromatography (GPC) measurement apparatus "Shodex GPC-101" manufactured by Showa Denko K.K. The conditions in measurement are shown below:

Column: Shodex HFIP-806M
Mobile phase solvent: hexafluoroisopropanol (HFIP) containing 2 mM sodium trifluoroacetate
Column temperature: 40° C.
Flow rate of mobile phase: 1.0 mL/min
Specimen concentration: about 0.1 mass %
Detector: IR detector
Amount of injection: 100 µm
Calibration curve: standard PMMA <Heat Aging Resistance Evaluation>

The polyimide resin was prepared in the form of a film having a thickness of 100 µm, thereafter introduced into an air-blowing constant-temperature thermostat "DN610" produced by Yamato Scientific Co., Ltd., and left to stand at 200° C. for 72 hours. The resulting film was subjected to GPC measurement, and the molecular weight (Mw, Mn) retention rates were determined from the respective changes in molecular weight before and after heating. The toughness of the film after heating was evaluated as follows: when the film was folded in half, a case where no breaking was observed at any position was rated as "A", a case where breaking was observed at any position and breaking was not observed at any position was rated as "B", and a case where breaking was observed at all positions was rated as "C".

The polyimide resin of the present invention can be subjected to, for example, depolymerization described below, and thus confirmed with respect to the compositional ratio of the monomers and the amount of introduction of the end group.

The depolymerization is performed as follows: 5 mL of a 1 M-sodium hydroxide solution obtained by mixing 4.0 g of sodium hydroxide, 50 mL of water and 50 mL of methanol is weighed, 100 mg of the resulting polyimide solid is added thereto, and thereafter the resulting mixture is heated in a pressure resistant container at 240° C. for 1 hour.

The obtained solution is subjected to an extraction operation with chloroform and water, and the solutions of monomers obtained by the depolymerization are separated. The monomers are separated by a column (HP-5) produced by Agilent Technologies with gas chromatography ("HP6890" produced by HP Development Company, L.P.) (in a heating condition where the temperature is kept at 50° C. for 10 minutes and thereafter increased to 300° C. at 10° C./min), and the area ratio of the respective monomers is calculated to thereby determine the compositional ratio of the monomers and the amount of introduction of the end group. The tetracarboxylic acid component is observed as a methyl ester.

It was confirmed by the method that the compositional ratio of the monomers and the amount of introduction of the end group of the polyimide resin of each of Examples and Comparative Examples of the present application corresponded to the molar ratio of the monomers and the compound for end group introduction loaded.

<Measurement of Thickness of Film>

The thickness of the film obtained in each of Examples 2a to 2d was measured at different 10 points in total with a micrometer, and the average value was defined as the actual measured thickness of the film.

<Measurement of Tensile Modulus and Tensile Strength>

A testing film of 100 mm×10 mm was cut out from the film obtained in each of Examples 2a to 2d, and used for measurement. The tensile test was performed with a tensile testing machine ("Strograph VG1E" produced by Toyo Seiki Seisaku-Sho, Ltd.) according to JIS K7127 at a temperature of 23° C. and a testing speed of 50 mm/min to measure the tensile modulus and the tensile strength. The film in each of Examples 2a to 2d was subjected to the tensile test in the MD direction.

<Measurement of Coefficient of Linear Thermal Expansion (CTE)>

A thermomechanical analysis apparatus (TMA/SS6100) produced by SII Nanotechnology, Inc. was used to perform TMA measurement of the polyimide resin film obtained in each of Examples 2a to 2d in a heating rate of 10° C./min to determine the CTE at 100 to 150° C. The film in each of Examples 2a to 2d was subjected to the measurement in the MD direction.

<Measurement of Haze Value, Yellow Index (YI) Value and Total Light Transmittance>

The haze value, the YI value and the total light transmittance of the film were measured with a spectral haze meter (Model: SH-7000 produced by Nippon Denshoku Kogyo Industries Co., Ltd.) according to a transmission method.

[Example 1] Production of Polyimide Resin 1

650 g of 2-(2-methoxyethoxy)ethanol (produced by Nippon Nyukazai Co., Ltd.) and 218.1 g (1.00 mol) of pyromellitic dianhydride (produced by Mitsubishi Gas Chemical Company, Inc.) were introduced in a 2 L separable flask equipped with a Dean-Stark apparatus, a Liebig condenser tube, a thermocouple, and a four-paddle blade. After creation of a nitrogen flow, the mixture was agitated at 150 rpm so as to become a homogeneous suspended solution. On the other hand, 70.60 g (0.496 mol) of 1,3-bis(aminomethyl)cyclohexane (produced by Mitsubishi Gas Chemical Company, Inc.), 46.13 g (0.397 mol) of 1,6-hexamethylenediamine (produced by Wako Pure Chemical Industries, Ltd.) and 19.88 g (0.0993 mol) of 4,4'-diaminodiphenyl ether (produced by Wakayama Seika Kogyo Co., Ltd.) were dissolved in 250 g of 2-(2-methoxyethoxy)ethanol with a 500 mL beaker, thereby preparing a mixed diamine solution. This mixed diamine solution was gradually added thereto with a plunger pump. The dropwise addition of the mixed diamine solution was carried out in a nitrogen flow state over the whole period. The number of rotations of the agitation blade was set to 250 rpm. After the completion of the dropwise addition, 65 g of 2-(2-methoxyethoxy)ethanol and 1.92 g (0.0149 mol) of n-octylamine (produced by Kanto Chemical Co., Inc.) as a compound for end group introduction were added thereto, and the mixture was further agitated. At this stage, a yellow polyamic acid solution was obtained. Next, the agitation speed was set to 200 rpm, and the polyamic acid solution in the 2 L separable flask was then heated to 190° C. In this heating process, the deposition of a polyimide resin powder and dehydration associated with imidization were confirmed at a solution temperature of from 130 to 140° C. The solution was kept at 190° C. for 30 minutes, then allowed to cool to room temperature, and filtered. The obtained polyimide resin powder was washed with 500 g of 2-(2-methoxyethoxy)ethanol and 500 g of methanol, filtered, and then dried at 190° C. for 10 hours with a drier, thereby providing 311 g of a powder of polyimide resin 1.

Polyimide resin 1 obtained was used to perform the measurements and evaluations. The results are shown in Table 2. The measurement of the IR spectrum of polyimide resin 1 showed the characteristic absorption of an imide ring $\nu(C=O)$ observed at 1771 and 1699 (cm$^{-1}$). A powder of polyimide resin 1 passed through sieves with a mesh opening of 500 μm in a proportion of 99 mass % or more and passed through sieves with a mesh opening of 250 μm in a proportion of 99 mass % or more according to the method of JIS K0069.

[Example 2] Production of Polyimide Resin 2

600 g of 2-(2-methoxyethoxy)ethanol (produced by Nippon Nyukazai Co., Ltd.) and 218.58 g (1.00 mol) of pyromellitic dianhydride (produced by Mitsubishi Gas Chemical Company, Inc.) were introduced in a 2 L separable flask equipped with a Dean-Stark apparatus, a Liebig condenser tube, a thermocouple, and a four-paddle blade. After creation of a nitrogen flow, the mixture was agitated at 150 rpm so as to become a homogeneous suspended solution. On the other hand, 49.42 g (0.347 mol) of 1,3-bis(aminomethyl)cyclohexane (produced by Mitsubishi Gas Chemical Company, Inc.) and 93.16 g (0.645 mol) of 1,8-octamethylenediamine (produced by Kanto Chemical Co., Inc.) were dissolved in 250 g of 2-(2-methoxyethoxy)ethanol with a 500 mL beaker, thereby preparing a mixed diamine solution. This mixed diamine solution was gradually added thereto with a plunger pump. The dropwise addition of the mixed diamine solution was carried out in a nitrogen flow state over the whole period. The number of rotations of the agitation blade was set to 250 rpm. After the completion of the dropwise addition, 130 g of 2-(2-methoxyethoxy)ethanol and 1.934 g (0.0149 mol) of n-octylamine (produced by Kanto Chemical Co., Inc.) as a compound for end group introduction were added thereto, and the mixture was further agitated. At this stage, a pale yellow polyamic acid solution was obtained. Next, the agitation speed was set to 200 rpm, and the polyamic acid solution in the 2 L separable flask was then heated to 190° C. In this heating process, the deposition of a polyimide resin powder and dehydration associated with imidization were confirmed at a solution temperature of from 120 to 140° C. The solution was kept at 190° C. for 30 minutes, then allowed to cool to room temperature, and filtered. The obtained polyimide resin powder was washed with 300 g of 2-(2-methoxyethoxy)ethanol and 300 g of methanol, filtered, and then dried at 180° C. for 10 hours with a drier, thereby providing 316 g of a powder of polyimide 2.

Polyimide resin 2 obtained was used to perform the measurements and evaluations. The results are shown in Table 2. The measurement of the IR spectrum of polyimide resin 2 showed the characteristic absorption of an imide ring $\nu(C=O)$ observed at 1768 and 1697 (cm$^{-1}$). A powder of polyimide resin 2 passed through sieves with a mesh opening of 500 μm in a proportion of 99 mass % or more and passed through sieves with a mesh opening of 250 μm in a proportion of 99 mass % or more according to the method of JIS K0069. In addition, the particle size was measured with a laser diffraction/light-scattering particle size distribution measuring instrument according to the aforementioned method, and exhibited a unimodal characteristic where the D10 was 9.3 μm, D50 was 14.5 μm and D90 was 22.7 μm, and the particle size distribution was confirmed to be narrow.

[Comparative Example 1] Production of Comparative Polyimide Resin 1

650 g of 2-(2-methoxyethoxy)ethanol (produced by Nippon Nyukazai Co., Ltd.) and 218.1 g (1.00 mol) of pyromellitic dianhydride (produced by Mitsubishi Gas Chemical Company, Inc.) were introduced in a 2 L separable flask equipped with a Dean-Stark apparatus, a Liebig condenser tube, a thermocouple, and a four-paddle blade. After creation of a nitrogen flow, the mixture was agitated at 150 rpm so as to become a homogeneous suspended solution. On the other hand, 70.60 g (0.496 mol) of 1,3-bis(aminomethyl)cyclohexane (produced by Mitsubishi Gas Chemical Company, Inc.), 46.13 g (0.397 mol) of 1,6-hexamethylenediamine (produced by Wako Pure Chemical Industries, Ltd.) and 19.88 g (0.0993 mol) of 4,4'-diaminodiphenyl ether (produced by Wakayama Seika Kogyo Co., Ltd.) were dissolved in 250 g of 2-(2-methoxyethoxy)ethanol with a 500 mL beaker, thereby preparing a mixed diamine solution. This mixed diamine solution was gradually added thereto with a plunger pump. The dropwise addition of the mixed diamine solution was carried out in a nitrogen flow state over the whole period. The number of rotations of the agitation blade was set to 250 rpm. After the completion of the dropwise addition, 65 g of 2-(2-methoxyethoxy)ethanol and 1.60 g (0.0149 mol) of benzylamine (produced by Kanto Chemical Co., Inc.) as a compound for end group introduction were added thereto, and the mixture was further agitated. At this stage, a yellow polyamic acid solution was obtained. Next, the agitation speed was set to 200 rpm, and the polyamic acid solution in the 2 L separable flask was then heated to 190° C. In this heating process, the deposition of a polyimide resin powder and dehydration associated with imidization were confirmed at a solution temperature of from 130 to 140° C. The solution was kept at 190° C. for 30 minutes, then allowed to cool to room temperature, and filtered. The obtained polyimide resin powder was washed with 500 g of 2-(2-methoxyethoxy)ethanol and 500 g of methanol, filtered, and then dried at 190° C. for 10 hours with a drier, thereby providing 310 g of a powder of comparative polyimide resin 1.

Comparative polyimide resin 1 obtained was used to perform the measurements and evaluations. The results are shown in Table 2. The measurement of the IR spectrum of comparative polyimide resin 1 showed the characteristic absorption of an imide ring $\nu(C=O)$ observed at 1771 and 1699 (cm$^{-1}$).

[Comparative Example 2] Production of Comparative Polyimide Resin 2

650 g of 2-(2-methoxyethoxy)ethanol (produced by Nippon Nyukazai Co., Ltd.) and 218.1 g (1.00 mol) of pyromellitic dianhydride (produced by Mitsubishi Gas Chemical Company, Inc.) were introduced in a 2 L separable flask equipped with a Dean-Stark apparatus, a Liebig condenser tube, a thermocouple, and a four-paddle blade. After creation of a nitrogen flow, the mixture was agitated at 150 rpm so as to become a homogeneous suspended solution. On the other hand, 70.24 g (0.494 mol) of 1,3-bis(aminomethyl)cyclohexane (produced by Mitsubishi Gas Chemical Company, Inc.), 45.90 g (0.395 mol) of 1,6-hexamethylenediamine (produced by Wako Pure Chemical Industries, Ltd.) and 19.77 g (0.0987 mol) of 4,4'-diaminodiphenyl ether (produced by Wakayama Seika Kogyo Co., Ltd.) were dissolved in 250 g of 2-(2-methoxyethoxy)ethanol with a 500 mL beaker, thereby preparing a mixed diamine solution. This mixed diamine solution was gradually added thereto with a plunger pump. The dropwise addition of the mixed diamine solution was carried out in a nitrogen flow state over the whole period. The number of rotations of the agitation blade was set to 250 rpm. After the completion of the dropwise addition, 65 g of 2-(2-methoxyethoxy)ethanol and 2.30 g (0.0247 mol) of aniline (produced by Kanto Chemical Co., Inc.) as a compound for end group introduction were added thereto, and the mixture was further agitated. At this stage, a yellow polyamic acid solution was obtained. Next, the agitation speed was set to 200 rpm, and the polyamic acid solution in the 2 L separable flask was then heated to 190° C. In this heating process, the deposition of a polyimide resin powder and dehydration associated with imidization were confirmed at a solution temperature of from 130 to 140° C. The solution was kept at 190° C. for 30 minutes, then allowed to cool to room temperature, and filtered. The obtained polyimide resin powder was washed with 500 g of 2-(2-methoxyethoxy)ethanol and 500 g of methanol, filtered, and then dried at 190° C. for 10 hours with a drier, thereby providing 308 g of a powder of comparative polyimide resin 2.

Comparative polyimide resin 2 obtained was used to perform the measurements and evaluations. The results are shown in Table 2. The measurement of the IR spectrum of comparative polyimide resin 2 showed the characteristic absorption of an imide ring $\nu(C=O)$ observed at 1771 and 1699 (cm$^{-1}$).

TABLE 1

| | Tetracarboxylic acid component (mol % in total tetracarboxylic acid components) | Diamine component (mol % in total diamine component) | | | | (1)/{(1) + (2)} (mol %) | End group | | |
|---|---|---|---|---|---|---|---|---|---|
| | | | | | | | Compound for end group introduction | End group | Amount, mol %* |
| | PMDA | 1,3-BAC | HMDA | OMDA | ODA | | | | |
| Example 1 | 100 | 50 | 40 | — | 10 | 56 | n-octylamine | n-octyl | 1.5 |
| Example 2 | 100 | 35 | — | 65 | — | 35 | n-octylamine | n-octyl | 1.5 |
| Comparative Example 1 | 100 | 50 | 40 | — | 10 | 56 | Benzylamine | Benzyl | 1.5 |
| Comparative Example 2 | 100 | 50 | 40 | — | 10 | 56 | Aniline | Phenyl | 2.5 |

*Amount of introduction of end group relative to total 100 mol % of total repeating structural units in polyimide resin (mol %)

Abbreviations in the Table are as follows.
PMDA; pyromellitic dianhydride
1,3-BAC; 1,3-bis(aminomethyl)cyclohexane
HMDA; 1,6-hexamethylenediamine
OMDA; 1,8-octamethylenediamine
ODA; 4,4'-diaminodiphenyl ether

TABLE 2

| | Physical properties of polyimide resin | | | | | | | Heat aging resistance | | | | |
|---|---|---|---|---|---|---|---|---|---|---|---|---|
| | Logarithmic viscosity (g/dL) | Tm (° C.) | Tg (° C.) | Tc (° C.) | Exothermic amount of crystallization (mJ/mg) | Crystallization half-time (sec) | Mw | Mn | 200° C. After 72 h Mw | 200° C. After 72 h Mn | Mw Retention rate (%) | Mn Retention rate (%) | Toughness of film |
| Example 1 | 0.69 | 338 | 229 | 309 | 12.3 | 20> | 18,700 | 7,000 | 21,000 | 6,200 | 112 | 89 | A |
| Example 2 | 0.96 | 319 | 184 | 266 | 20.1 | 20> | 39,800 | 10,000 | 40,500 | 8,800 | 102 | 88 | A |
| Comparative Example 1 | 0.63 | 337 | 227 | 306 | 12.2 | 20> | 19,200 | 6,900 | 17,400 | 5,600 | 91 | 81 | C |
| Comparative Example 2 | 0.61 | 336 | 227 | 307 | 12.1 | 20> | 18,300 | 7,300 | 16,700 | 5,200 | 91 | 71 | B |

As shown in Table 2, the polyimide resin of the present invention, containing a predetermined end group, is excellent in heat resistance and heat aging resistance.

Next, examples of production and evaluation of a stretched film of the polyimide resin of the present invention are shown.

[Example 2a] Production of Non-Stretched Film (Raw Material Roll Film)

Polyimide resin 2 obtained in Example 2 was melt-extruded at 330° C. with a biaxially screw extruder ("Labo Plasto Mill" produced by Toyo Seiki Seisaku-Sho, Ltd.), thereby producing a non-stretched film having a thickness of 90 µm according to a T-die/cooling roll method. The obtained film was used to perform various evaluations according to the aforementioned methods. The results are shown in Table 3.

[Examples 2b to 2d] Production of Stretched Film

The non-stretched film produced in Example 2a was cut out to a size of 100 mm×100 mm, and used as a raw material roll film. The raw material roll film was heated at 200° C. for 60 seconds for preheating, and thereafter simultaneously biaxially stretched with a biaxial stretching apparatus ("EX10-S5" produced by Toyo Seiki Seisaku-Sho, Ltd.). The stretching ratio, the stretching temperature and the stretching rate are as shown in Table 3. Next, the film stretched was heat-fixed at 230° C. for 10 minutes under strain, and thereafter cooled in air, thereby providing a stretched film of each of Examples 2b to 2d. The obtained film was used to perform various evaluations according to the aforementioned methods. The results are shown in Table 3.

TABLE 3

| | Stretching conditions | | | Film evaluation | | | | | | |
|---|---|---|---|---|---|---|---|---|---|---|
| | Stretching ratio MD × TD (times) | Stretching temperature (° C.) | Stretching rate (%/min.) | Thickness actually measured (µm) | Tensile modulus (GPa) | Tensile strength (MPa) | CTE (ppm) | Haze (%) | YI | Total light transmittance (%) |
| Example 2a | — | — | — | 90 | 1.9 | 74 | 56 | 11.9 | 11.3 | 85.8 |
| Example 2b | 1.3 × 1.3 | 200 | 1,000 | 56 | 2.3 | 97 | 43 | 5.87 | 7.0 | 87.3 |

TABLE 3-continued

| | Stretching conditions | | | Film evaluation | | | | | | |
|---|---|---|---|---|---|---|---|---|---|---|
| | Stretching ratio MD × TD (times) | Stretching temperature (° C.) | Stretching rate (%/min.) | Thickness actually measured (μm) | Tensile modulus (GPa) | Tensile strength (MPa) | CTE (ppm) | Haze (%) | YI | Total light transmittance (%) |
| Example 2c | 1.5 × 1.5 | 200 | 1,000 | 41 | 2.5 | 109 | 30 | 3.67 | 4.8 | 88.1 |
| Example 2d | 2.0 × 2.0 | 210 | 500 | 21 | 2.8 | 142 | 24 | 3.41 | 3.6 | 88.6 |

As shown in Table 3, the films of Examples 2a to 2d, each consisting of the polyimide resin of the present invention, have low haze value and YI value and have a high total light transmittance, and therefore all the films are excellent in appearance characteristics. The stretched films of Examples 2b to 2d each have higher mechanical strength, a lower coefficient of linear thermal expansion and also more excellent heat resistance than the non-stretched film of Example 2a.

INDUSTRIAL APPLICABILITY

The polyimide resin of the present invention is excellent in molding processability, heat resistance and heat aging resistance. For example, even if a film containing the polyimide resin is stored under a high-temperature environment of 200° C. or more for several days, the molecular weight retention rate is less decreased to allow the mechanical strength (toughness) of the film to be kept. The polyimide resin is preferably used in an application where heat aging resistance is required, for example, a member for use in automobiles, such as a gear, a tube and a pipe, a sliding member for use in a copier and the like, an industrial piping, an electronic member, and a covering material.

The invention claimed is:

1. A polyimide resin, comprising a repeating structural unit represented by formula (1) and a repeating structural unit represented by formula (2):

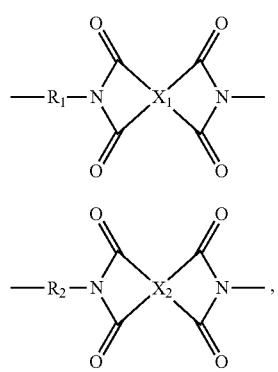

wherein:
a content ratio of the repeating structural unit of formula (1) with respect to a total of the repeating structural unit of formula (1) and the repeating structural unit of formula (2) is 20 to 70 mol %;
the polyimide resin has a chain aliphatic group having from 8 to 14 carbon atoms at an end thereof;
$R_1$ represents a divalent group represented by formula (R1-1) or (R1-2):

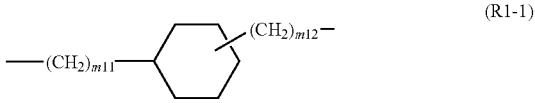

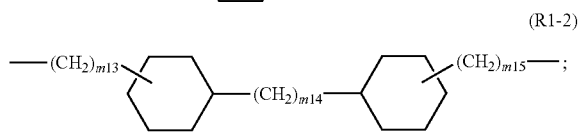

$m_{11}$ and $m_{12}$ each independently represent an integer of 0, 1 or 2;
$m_{13}$ to $m_{15}$ each independently represent an integer of 0, 1 or 2;
$R_2$ represents a divalent chain aliphatic group having from 5 to 16 carbon atoms; and
$X_1$ and $X_2$ each independently represent a tetravalent group having from 6 to 22 carbon atoms containing at least one aromatic ring.

2. The polyimide resin according to claim 1, wherein $R_1$ represents a divalent group represented by formula (R1-3):

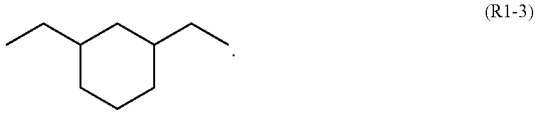

3. The polyimide resin according to claim 1, wherein $R_2$ represents an alkylene group having from 5 to 12 carbon atoms.

4. The polyimide resin according to claim 1, wherein:
$X_1$ and $X_2$ each independently represent a tetravalent group represented by one of formulae (X-1) to (X-4):

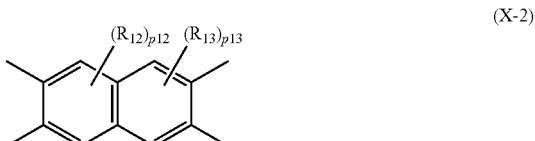

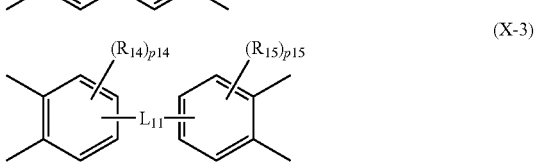

-continued

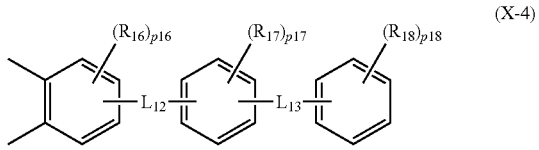
(X-4)

$R_{11}$ to $R_{18}$ each independently represent an alkyl group having from 1 to 4 carbon atoms;

$p_{11}$ to $p_{13}$ each independently represent an integer of 0, 1 or 2;

$p_{14}$, $p_{15}$, $p_{16}$ and $p_{18}$ each independently represent an integer of 0, 1, 2 or 3;

$p_{17}$ represents an integer of 0, 1, 2, 3 or 4; and $L_{11}$ to $L_{13}$ each independently represent a single bond, an ether group, a carbonyl group, or an alkylene group having from 1 to 4 carbon atoms.

5. The polyimide resin according to claim 1, further comprising a repeating structural unit represented by formula (3):

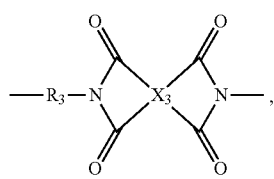
(3)

wherein:
a content ratio of the repeating structural unit of formula (3) with respect to the total of the repeating structural unit of formula (1) and the repeating structural unit of formula (2) is 25 mol % or less;
$R_3$ represents a divalent group having from 6 to 22 carbon atoms containing at least one aromatic ring; and
$X_3$ represents a tetravalent group having from 6 to 22 carbon atoms containing at least one aromatic ring.

6. The polyimide resin according to claim 1, wherein a content of the chain aliphatic group having from 8 to 14 carbon atoms is 0.01 mol % or more and 10 mol % or less based on 100 mol % of total repeating structural units in the polyimide resin.

7. A method for producing the polyimide resin according to claim 1, the method comprising mixing a tetracarboxylic acid component and a diamine component, and then further mixing and reacting a compound having a chain aliphatic group having from 8 to 14 carbon atoms, to obtain the polyimide resin.

8. The method according to claim 7, wherein the compound having a chain aliphatic group having from 8 to 14 carbon atoms is a monoamine.

9. A molded article, comprising the polyimide resin according to claim 1.

10. The molded article according to claim 9, comprising a thin portion having a thickness of 1000 μm or less.

11. The polyimide resin according to claim 1, wherein the chain aliphatic group has from 8 to 12 carbon atom.

12. The polyimide resin according to claim 1, further comprising a repeating structural unit represented by formula (4):

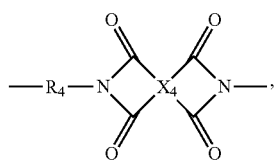
(4)

wherein:
$R_4$ represents a divalent group containing —$SO_2$— or —$Si(R_x)(R_y)O$—;
$R_x$ and $R_y$ each independently represent a chain aliphatic group having from 1 to 3 carbon atoms, or a phenyl group; and
$X_4$ represents a tetravalent group having from 6 to 22 carbon atoms containing at least one aromatic ring.

* * * * *